(12) United States Patent
Farmer et al.

(10) Patent No.: US 6,909,000 B2
(45) Date of Patent: Jun. 21, 2005

(54) BRIDGED BICYCLIC SERINE PROTEASE INHIBITORS

(75) Inventors: Luc J. Farmer, Foxborough, MA (US); Janos Pitlik, Westborough, MA (US); Robert B. Perni, Marlborough, MA (US); Lawrence F. Courtney, Medway, MA (US); John van Drie, Andover, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 173 days.

(21) Appl. No.: 10/193,048

(22) Filed: Jul. 11, 2002

(65) Prior Publication Data

US 2003/0119752 A1 Jun. 26, 2003

Related U.S. Application Data

(60) Provisional application No. 60/322,714, filed on Sep. 17, 2001, and provisional application No. 60/304,615, filed on Jul. 11, 2001.

(51) Int. Cl.$^7$ .................. C07D 241/10; C07D 209/02; A61K 31/4965; A61K 31/40
(52) U.S. Cl. .................. 544/406; 548/312.1; 548/452; 548/515; 514/255.05; 514/397; 514/412; 514/413
(58) Field of Search .................. 544/406; 548/312.1, 548/452, 515; 514/255.05, 39, 412, 413, 252.1, 397

(56) References Cited

U.S. PATENT DOCUMENTS

| | | | |
|---|---|---|---|
| 4,720,484 A | 1/1988 | Vincent et al. | |
| 6,265,380 B1 * | 7/2001 | Tung et al. | .................. 514/17 |

FOREIGN PATENT DOCUMENTS

| | | |
|---|---|---|
| WO | WO 97/43310 | 11/1997 |
| WO | WO 98/17679 | 4/1998 |
| WO | WO 98/46630 | 10/1998 |
| WO | WO 99/07733 | 2/1999 |
| WO | WO 99/07734 | 2/1999 |
| WO | WO 99/50230 | 10/1999 |
| WO | WO 99/64442 | 12/1999 |
| WO | WO 00/09543 | 2/2000 |
| WO | WO 00/09558 | 2/2000 |
| WO | WO 01/74768 A2 | 10/2001 |
| WO | WO 02/08244 A2 | 1/2002 |

OTHER PUBLICATIONS

LaPlante, S.R., et al., "NMR Line–Broadening and Transferred NOESY as a Medicinal Chemistry Tool for Studying Inhibitors of the Hepatits C Virus NS3 Protease Domain," *Bioorg. & Med. Chem. Ltrs.*, 10:2271–2274 (2000).

Llinàs–Brunet, M., et al., "Highly Potent and Selective Peptide–Based Inhibitors of the Hepatitis C Virus Serine Protease: Towards Smaller Inhibitors," *Bioorg. & Med. Chem. Ltrs.*, 10:2267–2270 (2000).

Dunsdon, R. M., et al., "Solid Phase Synthesis of Aminoboronic Acids: Potent Inhibitors of the Hepatitis C Virus NS3 Proteinase," *Bioorg. & Med. Chem. Ltrs.*, 10:1577–1579 (2000).

Han, W., et al., "α–Ketoamides, α–Ketoesters and α–Diketones as HCV NS3 Protease Inhibitors," *Bioorg. & Med. Chem. Ltrs.*, 10:711–713 (2000).

Llinàs–Brunet, M., et al., "Peptide–Based Inhibitors of the Hepatitis C Virus Serine Protease," *Bioorg. & Med. Chem. Ltrs.*, 8:1713–1718 (1998).

* cited by examiner

*Primary Examiner*—Shailendra Kumar
(74) *Attorney, Agent, or Firm*—Michael C. Badia; Vertex Pharmaceuticals Incorporated

(57) ABSTRACT

The present invention relates to peptidomimetic compounds which inhibit serine protease activity, particularly the activity of hepatitis C virus NS3-NS4A protease. As such, they act by interfering with the life cycle of the hepatitis C virus and are also useful as antiviral agents. The compounds of this invention have a bridged bicyclic moiety at the P2 position. The invention further relates to compositions comprising these compounds either for ex vivo use or for administration to a patient suffering from HCV infection. The invention also relates to methods of treating an HCV infection in a patient by administering a composition comprising a compound of this invention.

46 Claims, No Drawings

BRIDGED BICYCLIC SERINE PROTEASE INHIBITORS

This application claims benefit of 60/304,615, filed Jul. 11, 2001, and claims benefit of 60/322,714, filed Sep. 17, 2001.

TECHNICAL FIELD OF THE INVENTION

The present invention relates to peptidomimetic compounds which inhibit serine protease activity, particularly the activity of hepatitis C virus NS3-NS4A protease. As such, they act by interfering with the life cycle of the hepatitis C virus and are also useful as antiviral agents. The compounds of this invention are characterized by a bridged bicyclic moiety at the P2 position. The invention further relates to compositions comprising these compounds either for ex vivo use or for administration to a patient suffering from HCV infection. The invention also relates to methods of treating an HCV infection in a patient by administering a composition comprising a compound of this invention.

BACKGROUND OF THE INVENTION

Infection by hepatitis C virus ("HCV") is a compelling human medical problem. HCV is recognized as the causative agent for most cases of non-A, non-B hepatitis, with an estimated human seroprevalence of 3% globally [A. Alberti et al., "Natural History of Hepatitis C," *J. Hepatology*, 31., (Suppl. 1), pp. 17–24 (1999)]. Nearly four million individuals may be infected in the United States alone [M. .J. Alter et al., "The Epidemiology of Viral Hepatitis in the United States, *Gastroenterol. Clin. North Am.,* 23, pp. 437–455 (1994); M. J. Alter "Hepatitis C Virus Infection in the United States," *J. Hepatology,* 31., (Suppl. 1), pp. 88–91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," *FEMS Microbiology Reviews,* 14, pp. 201–204 (1994); D. Lavanchy, "Global Surveillance and Control of Hepatitis C," *J. Viral Hepatitis,* 6, pp. 35–47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", *FEMS Microbiology Reviews,* 14, pp. 211–220 (1994); I. Saito et. al., "Hepatitis C Virus Infection is Associated with the Development of Hepatocellular Carcinoma," *Proc. Natl. Acad. Sci. USA,* 87, pp. 6547–6549 (1990)]. Unfortunately, there are no broadly effective treatments for the debilitating progression of chronic HCV.

The HCV genome encodes a polyprotein of 3010–3033 amino acids [Q.-L. Choo, et. al., "Genetic Organization and Diversity of the Hepatitis C Virus."*Proc. Natl. Acad. Sci. USA,* 88, pp. 2451–2455 (1991); N. Kato et al., "Molecular Cloning of the Human Hepatitis C Virus Genome From Japanese Patients with Non-A, Non-B Hepatitis," *Proc. Natl. Acad. Sci. USA,* 87, pp. 9524–9528 (1990); A. Takamizawa et. al., "Structure and Organization of the Hepatitis C Virus Genome Isolated From Human Carriers," *J. Virol.,* 65, pp. 1105–1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," *J. Virol.,* 67, pp. 3835–3844 (1993); A. Grakoui et. al., "Characterization of the Hepatitis C Virus-Encoded Serine Proteinase: Determination of Proteinase-Dependent Polyprotein Cleavage Sites," *J. Virol.,* 67, pp. 2832–2843 (1993); A. Grakoui et. al., "Expression and Identification of Hepatitis C Virus Polyprotein Cleavage Products," *J. Virol.,* 67, pp. 1385–1395 (1993); L. Tomei et. al., "NS3 is a serine protease required for processing of hepatitis C virus polyprotein", *J. Virol.,* 67, pp. 4017–4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decreases viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA,* 87, pp. 8898–8902 (1990)]. The first 181 amino acids of NS3 (residues 1027–1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", *J. Virol.,* 68, pp. 8147–8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing HIV protease inhibitors, which inhibit viral protein processing are potent antiviral agents in man, indicating that interrupting this stage of the viral life cycle results in therapeutically active agents. Consequently it is an attractive target for drug discovery.

Several potential HCV protease inhibitors have been described in the prior art [PCT publication Nos. WO 00/09558, WO 00/09543, WO 99/64442, WO 99/07733, WO 99/07734, WO 99/50230, WO 98/46630, WO 98/17679 and WO 97/43310, U.S. Pat. No. 5,990,276, M. Llinas-Brunet et al., *Bioorg. Med. Chem. Lett.,* 8, pp. 1713–18 (1998); W. Han et al., *Bioorg. Med. Chem. Lett.,* 10, 711–13 (2000); R. Dunsdon et al., *Bioorg. Med. Chem. Lett.,* 10, pp. 1571–79 (2000); M. Llinas-Brunet et al., *Bioorg. Med. Chem. Lett.,* 10, pp. 2267–70 (2000); and S. LaPlante et al., *Bioorg. Med. Chem. Lett.,* 10, pp. 2271–74 (2000)]. Unfortunately, there are no serine protease inhibitors available currently as anti-HCV agents.

Furthermore, the current understanding of HCV has not led to any other satisfactory anti-HCV agents or treatments. The only established therapy for HCV disease is interferon treatment. However, interferons have significant side effects [M. A. Wlaker et al., "Hepatitis C Virus: An Overview of Current Approaches and Progress," *DDT,* 4, pp. 518–29 (1999); D. Moradpour et al., "Current and Evolving Therapies for Hepatitis C," *Eur. J. Gastroenterol. Hepatol.,* 11, pp. 1199–1202 (1999); H. L. A. Janssen et al. "Suicide Associated with Alfa-Interferon Therapy for Chronic Viral Hepatitis," *J. Hepatol.,* 21, pp. 241–243 (1994); P. F. Renault et al., "Side Effects of Alpha Interferon," *Seminars in Liver Disease,* 9, pp. 273–277. (1989)] and induce long term remission in only a fraction (~25%) of cases [O. Weiland, "Interferon Therapy in Chronic Hepatitis C Virus Infection", *FEMS Microbiol. Rev.,* 14, pp. 279–288 (1994)]. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

The present invention solves the problem set forth above by providing a compound of formula I:

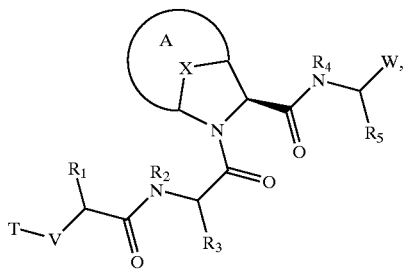

(I)

wherein:
A, together with X and the atoms to which X is bound, is a 4- to 7-membered aromatic or non-aromatic ring having up to 4 heteroatoms independently selected from N, NH, O, SO, or $SO_2$; wherein said ring is optionally fused to a (C6–C10)aryl, (C5–C10) heteroaryl, (C3–C10) cycloalkyl or (C3–C10) heterocyclyl; wherein A has up to 3 substituents selected independently from J;

X is —$[CH_2]_o$—, —$[CJ'J']_o$—, —$[CH_2]_m$—O—, —$[CH_2]_m$—$S(O)_2$—, —$[CH_2]_m$—SO—, —$[CH_2]_m$—S—, —$[CR_{20}R_{20}]_m$—$NR_{21}$—, or —$[CR_{20}R_{20}]_m$—NJ"—, wherein:
$R_{21}$ is hydrogen or —C(O)—O—$R_{22}$;
o is 1 or 2;
$R_{22}$ is —(C1–C6)alkyl, —(C2–C6)alkenyl, or —(C2–C6) alkynyl;
m is 0 or 1;
J is halogen, —OR', —$NO_2$, —$CF_3$, —$OCF_3$, —R', oxo, —OR', —O-benzyl, —O-phenyl, 1,2-methylenedioxy, —$N(R')_2$, —SR', —SOR', —$SO_2R'$, —C(O)R', —COOR', or —$CON(R')_2$;
J' is halogen, —OR', —$NO_2$, —$CF_3$, —$OCF_3$, —R', —OR', —O-benzyl, —O-phenyl, 1,2-methylenedioxy, —$N(R')_2$, —SR', —SOR', —$SO_2R'$, —C(O)R', —COOR', or —$CON(R')_2$;
J" is —OR', —$CF_3$, —$OCF_3$, —R', oxo, —OR', —O-benzyl, —O-phenyl, 1,2-methylenedioxy, —$N(R')_2$, —SR', —SOR', —$SO_2R'$, —C(O)R', —COOR', or —$CON(R')_2$, wherein each R' is independently:
hydrogen,
—(C1–C12) aliphatic,
—(C3–C10)cycloalkyl or -cycloalkenyl,
—(C1–C12)aliphatic-[(C3–C10)cycloalkyl or -cycloalkenyl],
—(C6–C10)aryl,
—(C1–C12)aliphatic-(C6–C10)aryl,
—(C3–C10)heterocyclyl,
—(C1–C12)aliphatic-(C6–C10)heterocyclyl,
—(C5–C10)-heteroaryl, or
—(C1–C12)-aliphatic-(C5–C10)heteroaryl;

$R_1$ and $R_3$ are independently:
—(C1–C12)aliphatic,
—(C3–C10)-cycloalkyl or -cycloalkenyl,
—(C1–C12)-aliphatic-[(C3–C10)-cycloalkyl or -cycloalkenyl],
—(C6–C10)-aryl,
(C1–C12)aliphatic-(C6–C10)aryl,
—(C3–C10)-heterocyclyl,
—(C1–C12)aliphatic-(C6–C10)heterocyclyl,
—(C5–C10)heteroaryl, or
—(C1–C12)aliphatic-(C5–C10)heteroaryl,
wherein each of $R_1$ and $R_3$ is independently and optionally substituted with up to 3 substituents independently selected from J;
wherein up to 3 aliphatic carbon atoms in $R_1$ and $R_3$ may be replaced by a heteroatom selected from O, NH, S, SO, and $SO_2$ in a chemically stable arrangement;
$R_2$ and $R_4$ are independently
hydrogen,
—(C1–C12)aliphatic,
—(C1–C12)aliphatic-(C3–C10)cycloalkyl, or
—(C1–C12)aliphatic-(C6–C10)aryl,
wherein each of $R_2$ and $R_4$ is independently and optionally substituted with up to 3 substituents independently selected from J;
wherein up to two aliphatic carbon atoms in $R_2$ and $R_4$ may be replaced by a heteroatom selected from O, NH, S, SO, and $SO_2$;
$R_5$ is —(C1–C12)aliphatic, wherein any hydrogen is optionally replaced with halogen, and wherein any hydrogen or halogen atom bound to any terminal carbon atom of $R_5$ is optionally substituted with sulfhydryl or hydroxy;
W is: —C(O)OH;

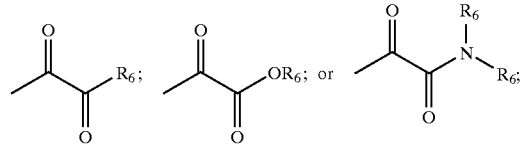

wherein each $R_6$ is independently:
hydrogen,
—(C1–C12)aliphatic,
—(C6–C10)aryl,
—(C6–C10)aryl-(C1–C12)aliphatic,
—(C3–C10)-cycloalkyl or -cycloalkenyl,
—(C1–C12)-aliphatic-[(C3–C10)-cycloalkyl or -cycloalkenyl],
—(C3–C10)heterocyclyl,
—(C3–C10)heterocyclyl-(C1–C12)aliphatic,
—(C5–C10)heteroaryl, or
—(C1–C12)aliphatic-(C5–C10)heteroaryl, or
two $R_6$ groups, which are bound to the same nitrogen atom, form together with that nitrogen atom, a —(C3–C10) heterocyclic ring;
wherein $R_6$ is optionally substituted with up to 3 J substituents or with a suitable electron withdrawing group;
V is —$C(O)N(R_8)$—, —$S(O)N(R_8)$—, —$S(O)_2N(R_8)$—, a bond, —$CH(R_8)$—, —$N(R_8)$—, —O—, —O—$CH(R_8)$—, —S—, —S—$CH(R_8)$, —C(O)—, —C(O)—O—, —C(O)—S—, —C(O)—$CHR_8$—, —S(O)—, —S(O)—$CH(R_8)$, —S(O)—N($R_8$)—CHR$_8$, —S(O)$_2$—, —S—(O)$_2$—CH(R$_8$)—, or —S(O)$_2$—N(R$_8$)—CHR$_8$;
wherein R$_8$ is hydrogen or —(C1–C12)aliphatic;
T is:
- —(C6–C10)aryl,
- —(C1–C12)aliphatic-(C6–C10)aryl,
- —(C3–C10)-cycloalkyl or -cycloalkenyl,
- —(C1–C12)aliphatic-[(C3–C10)-cycloalkyl or -cycloalkenyl],
- —(C3–C10)heterocyclyl,
- —(C1–C12)aliphatic-(C3–C10)heterocyclyl,
- —(C5–C10)heteroaryl, or
- —(C1–C12)aliphatic- (C5–C10)heteroaryl; or T is:

[Chemical structures showing various T group options with R$_{10}$, K substituents including sulfonamide, carbamate, urea, sulfamide, hydroxyl, and thiol groups]

wherein:
R$_{10}$ is:
hydrogen,
- —(C1–C12)aliphatic,
- —(C6–C10)aryl,
- —(C1–C12)aliphatic-(C6–C10)aryl,
- —(C3–C10)-cycloalkyl or -cycloalkenyl,
- —(C1–C12)aliphatic-[(C3–C10)-cycloalkyl or -cycloalkenyl],
- —(C3–C10)heterocyclyl,
- —(C1–C12)aliphatic-(C3–C10)heterocyclyl,
- —(C5–C10)heteroaryl, or
- —(C1–C12)aliphatic-(C5–C10)heteroaryl, wherein each T is optionally substituted with up to 3 J substituents;
K is a bond, —(C1–C12)aliphatic, —O—, —S—, —NR$_9$—, —C(O)—, or —C(O)—NR$_9$—, wherein R$_9$ is hydrogen or —(C1–C12) aliphatic;
n is 1–3; and
each R$_{20}$ is independently hydrogen, —(C1–C6)aliphatic or —O—((C1–C6)aliphatic); or each R$_{20}$ is taken together with the carbon atoms to which they are bound to form a (C3–C6)cycloalkyl.

The invention also relates to compositions that comprise the above compound and the use thereof. Such compositions may be useful to pre-treat invasive devices to be inserted into a patient, to treat biologicals, such as blood, prior to administration to a patient, and for direct administration to a patient. In each case the composition will be used to inhibit HCV replication and to lessen the risk of or the severity of HCV infection.

DETAILED DESCRIPTION OF THE INVENTION

The present invention provides a compound of (I)

[Chemical structure of formula (I) showing a bicyclic ring system with substituents A, X, W, R$_1$, R$_2$, R$_3$, R$_4$, R$_5$, T, V]

formula (I):
wherein:
A, together with X and the atoms to which X is bound, is a 4- to 7-membered aromatic or non-aromatic ring having up to 4 heteroatoms independently selected from N, NH, O, SO, or SO$_2$; wherein said ring is optionally fused to a (C6–C10) aryl, (C5–C10)heteroaryl, (C3–C10) cycloalkyl or (C3–C10)heterocyclyl; wherein A has up to 3 substituents selected independently from J;
X is —[CH$_2$]$_o$—, —[CJ'J']$_o$—, —[CH$_2$]$_m$—O—, —[CH$_2$]$_m$—S(O)$_2$—, —[CH$_2$]$_m$—SO—, —[CH$_2$]$_m$—S—, —[CR$_{20}$R$_{20}$]$_m$—NR$_{21}$—, or —[CR$_{20}$R$_{20}$]$_m$—NJ''—, wherein:
R$_{21}$ is hydrogen or —C(O)—O—R$_{22}$;
o is 1 or 2;
R$_{22}$ is —(C1–C6)alkyl, —(C2–C6)alkenyl, or —(C2–C6)alkynyl;
m is 0 or 1;
J is halogen, —OR', —NO$_2$, —CF$_3$, —OCF$_3$, —R', oxo, —OR', —O-benzyl, —O-phenyl, 1,2-methylenedioxy, —N(R')$_2$, —SR', —SOR', —SO$_2$R', —C(O)R', —COOR', or —CON(R')$_2$;
J' is halogen, —OR', —NO$_2$, —CF$_3$, —OCF$_3$, —R', —OR', —O-benzyl, —O-phenyl, 1,2-methylenedioxy, —N(R')$_2$, —SR', —SOR', —SO$_2$R', —C(O)R', —COOR', or —CON(R')$_2$;
J'' is —OR', —CF$_3$, —OCF$_3$, —R', oxo, —OR', —O-benzyl, —O-phenyl, 1,2-methylenedioxy, —N(R')$_2$, —SR', —SOR', —SO$_2$R', —C(O)R', —COOR', or —CON(R')$_2$, wherein each R' is independently:
hydrogen, —(C1–C12) aliphatic,
—(C3–C10)cycloalkyl or -cycloalkenyl,
—(C1–C12)aliphatic-[(C3–C10)cycloalkyl or -cycloalkenyl],
—(C6–C10)aryl,
—(C1–C12)aliphatic-(C6–C10)aryl,
—(C3–C10)heterocyclyl,
—(C1–C12)aliphatic-(C6–C10)heterocyclyl,
—(C5–C10)-heteroaryl, or
—(C1–C12)-aliphatic-(C5–C10)heteroaryl;
$R_1$ and $R_3$ are independently:
—(C1–C12)aliphatic,
—(C3–C10)-cycloalkyl or -cycloalkenyl,
—(C1–C12)-aliphatic-[(C3–C10)-cycloalkyl or -cycloalkenyl],
—(C6–C10)-aryl,
(C1–C12)aliphatic-(C6–C10)aryl,
—(C3–C10)-heterocyclyl,
—(C1–C12)aliphatic-(C6–C10)heterocyclyl,
—(C5–C10)heteroaryl, or
—(C1–C12)aliphatic-(C5–C10)heteroaryl,
wherein each of $R_1$ and $R_3$ is independently and optionally substituted with up to 3 substituents independently selected from J;
wherein up to 3 aliphatic carbon atoms in $R_1$ and $R_3$ may be replaced by a heteroatom selected from O, NH, S, SO, and $SO_2$ in a chemically stable arrangement;
$R_2$ and $R_4$ are independently
hydrogen,
—(C1–C12)aliphatic,
—(C1–C12)aliphatic-(C3–C10)cycloalkyl, or
—(C1–C12)aliphatic-(C6–C10)aryl,
wherein each of $R_2$ and $R_4$ is independently and optionally substituted with up to 3 substituents independently selected from J;
wherein up to two aliphatic carbon atoms in $R_2$ and $R_4$ may be replaced by a heteroatom selected from O, NH, S, SO, and $SO_2$;
$R_5$ is —(C1–C12)aliphatic, wherein any hydrogen is optionally replaced with halogen, and wherein any hydrogen or halogen atom bound to any terminal carbon atom of $R_5$ is optionally substituted with sulfhydryl or hydroxy;
W is: —C(O)OH;

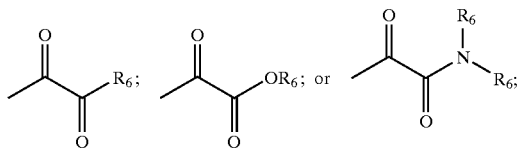

wherein each $R_6$ is independently:
hydrogen,
—(C1–C12)aliphatic,
—(C6–C10)aryl,
—(C6–C10)aryl-(C1–C12)aliphatic,
—(C3–C10)-cycloalkyl or -cycloalkenyl,
—(C1–C12)-aliphatic-[(C3–C10)-cycloalkyl or -cycloalkenyl],
—(C3–C10)heterocyclyl,
—(C3–C10)heterocyclyl-(C1–C12)aliphatic,
—(C5–C10)heteroaryl, or
—(C1–C12)aliphatic-(C5–C10)heteroaryl, or
two $R_6$ groups, which are bound to the same nitrogen atom, form together with that nitrogen atom, a —(C3–C10) heterocyclic ring;
wherein $R_6$ is optionally substituted with up to 3 J substituents or with a suitable electron withdrawing group;
V is —C(O)N($R_8$)—, —S(O)N($R_8$)—, —S(O)$_2$N($R_8$)—, a bond, —CH($R_8$)—, —N($R_8$)—, —O—, —O—CH($R_8$)—, —S—, —S—CH($R_8$), —C(O)—, —C(O)—O—, —C(O)—S—, —C(O)—CHR$_8$—, —S(O)—, —S(O)—CH($R_8$), —S(O)—N($R_8$)—CHR$_8$, —S(O)$_2$—, —S—(O)$_2$—CH($R_8$)—, or —S(O)$_2$—N($R_8$)—CHR$_8$;
wherein $R_8$ is hydrogen or —(C1–C12)aliphatic;
T is:
—(C6–C10)aryl,
—(C1–C12)aliphatic-(C6–C10)aryl,
—(C3–C10)-cycloalkyl or -cycloalkenyl,
—(C1–C12)aliphatic-[(C3–C10)-cycloalkyl or -cycloalkenyl],
—(C3–C10)heterocyclyl,
—(C1–C12)aliphatic-(C3–C10)heterocyclyl,
—(C5–C10)heteroaryl, or
—(C1–C12)aliphatic-(C5–C10)heteroaryl; or
T is:

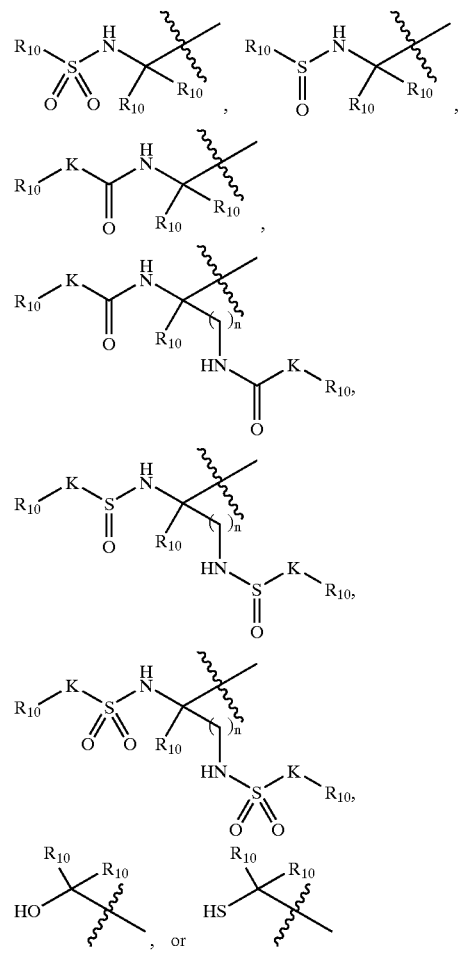

wherein:
$R_{10}$ is:

hydrogen,
—(C1–C12)aliphatic,
—(C6–C10)aryl,
—(C1–C12)aliphatic-(C6–C10)aryl,
—(C3–C10)-cycloalkyl or -cycloalkenyl,
—(C1–C12)aliphatic-[(C3–C10)-cycloalkyl or -cycloalkenyl],
—(C3–C10)heterocyclyl,
—(C1–C12)aliphatic-(C3–C10)heterocyclyl,
—(C5–C10)heteroaryl, or
—(C1–C12)aliphatic-(C5–C10)heteroaryl,
wherein each T is optionally substituted with up to 3 J substituents;

K is a bond, —(C1–C12)aliphatic, —O—, —S—, —$NR_9$—, —C(O)—, or —C(O)—$NR_9$—, wherein $R_9$ is hydrogen or —(C1–C12)aliphatic;

n is 1–3; and each $R_{20}$ is independently hydrogen, —(C1–C6)aliphatic or —O—((C1–C6)aliphatic); or each $R_{20}$ is taken together with the carbon atoms to which they are bound to form a (C3–C6)cycloalkyl.

Definitions

The term "aryl" as used herein means a monocyclic or bicyclic carbocyclic aromatic ring system. Phenyl is an example of a monocyclic aromatic ring system. Bicyclic aromatic ring systems include systems wherein both rings are aromatic, e.g., naphthyl, and systems wherein only one of the two rings is aromatic, e.g., tetralin.

The bond " - - - " refers to an optionally present bond.

The term "heterocyclyl" as used herein means a monocyclic or bicyclic non-aromatic ring system having up to 4, and preferably 1 to 3, heteroatom or heteroatom groups in each ring selected from O, N, NH, S, SO, or $SO_2$ in a chemically stable arrangement. In a bicyclic non-aromatic ring system embodiment of "heterocyclyl" one or both rings may contain said heteroatom or heteroatom groups.

Heterocyclic rings include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, and benzodithiane.

The term "heteroaryl" as used herein means a monocyclic or bicyclic aromatic ring system having up to 4, and preferably 1 to 3, heteroatom or heteroatom groups in each ring selected from O, N, NH or S in a chemically stable arrangement. In such a bicyclic aromatic ring system embodiment of "heteroaryl":
one or both rings may be aromatic; and
one or both rings may contain said heteroatom or heteroatom groups.

Heteroaryl rings include 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

Each of the above aryl, heterocyclyl or heteroaryl above may contain up to 3 substituents independently selected from halogen, —OR', —$NO_2$, —$CF_3$, —$OCF_3$, —R', oxo, —OR', —O-benzyl, —O-phenyl, 1,2-methylenedioxy, —N(R')$_2$, —C(O)R', —COOR' or —CON(R')$_2$, wherein R' is independently selected from H, (C1–C6)— alkyl, (C2–C6)-alkenyl or alkynyl.

The term "aliphatic" as used herein means a straight chained or branched alkyl, alkenyl or alkynyl. It is understood that alkenyl or alkynyl embodiments need at least two carbon atoms in the aliphatic chain.

The term "cycloalkyl or cycloalkenyl", refers to a monocyclic or fused or bridged bicyclic carbocyclic ring system that is not aromatic. Cycloalkenyl rings have one or more units of unsaturation. Preferred cycloalkyl groups include cyclopropyl, cyclobutyl, cyclopentyl, cyclohexyl, cyclohexenyl, cycloheptyl, cycloheptenyl, nornbornyl, adamantyl and decalin-yl.

The phrase "chemically stable arrangement" as used herein refers to a compound structure that renders the compound sufficiently stable to allow manufacture and administration to a mammal by methods known in the art. Typically, such compounds are stable at a temperature of 40° C. or less, in the absence of moisture or other chemically reactive condition, for at least a week.

According to a preferred embodiment, ring A together with X and the atoms to which X is bound, has up to 3 heteroatoms independently selected from N, NH, O, SO, and $SO_2$.

According to a preferred embodiment, ring A together with X and the atoms to which X is bound, is a 3–6 membered carbocyclic non-aromatic or aromatic ring. More preferably, ring A, together with X and the atoms to which X is bound, is cyclopropyl, cyclobutyl, cyclopentyl, cyclohexyl or phenyl. Even more preferably, ring A, together with X and the atoms to which X is bound, is cylcohexyl or cyclopentyl. Most preferably, ring A, together with X and the atoms to which X is bound, is cyclohexyl.

According to another preferred embodiment, ring A, together with X and the atoms to which X is bound, is a 3–6 membered heterocyclic ring. More preferably, ring A together with X and the atoms to which X is bound, is a 5–6 membered heterocyclic ring.

According to another preferred embodiment, ring A together with X and the atoms to which X is bound, is a 5–6 membered heteroaryl ring.

According to yet another preferred embodiment, ring A, together with X and the atoms to which X is bound, is fused to a (C6–C10)aryl, (C5–C10)heteroaryl, (C3–C10) cycloalkyl or (C3–C10)— heterocyclyl. Preferably, ring A together with X and the atoms to which X is bound, is fused to cyclohexyl, cyclopentyl, phenyl or pyridyl.

According to a preferred embodiment, compounds of the present invention have formula (IA):

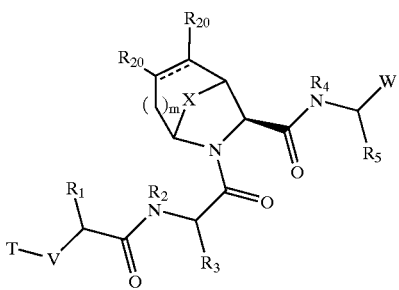

wherein T, V, $R_1$, $R_2$, $R_3$, $R_4$, $R_5$, $R_{20}$, X, W, and m are as defined herein.

According to another preferred embodiment, compounds of the present invention have formula (IB):

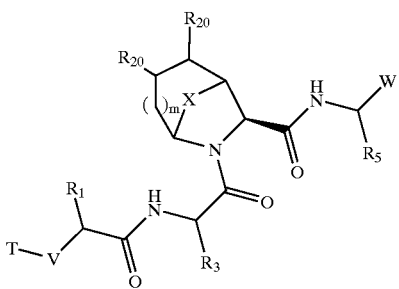

wherein T, V, $R_1$, $R_3$, $R_5$, $R_{20}$, X, W and m are as defined herein.

According to a preferred embodiment, V is —NH—.

According to another preferred embodiment, V is —C(O)—.

According to another preferred embodiment, $R_5$ is C2–C3 alkyl substituted with 1–3 chlorine or fluorine.

According to yet another preferred embodiment T or $R^6$ is a heterocyclyl or heteroaryl, optionally having up to 3 substituents as defined above.

According to yet another preferred embodiment, T is a —(C5–C10)heteroaryl.

According to yet another preferred embodiment, T is selected from 3-1H-benzimidazol-2-one, 3-(1-alkyl)-benzimidazol-2-one, 2-tetrahydrofuranyl, 3-tetrahydrofuranyl, pyrazolinyl, 1,3-dihydro-imidazol-2-one, 2-imidazolyl, 4-imidazolyl, 5-imidazolyl, 2-oxazolyl, 4-oxazolyl, 5-oxazolyl, 2-pyrrolyl, 3-pyrrolyl, 2-pyrimidinyl, 4-pyrimidinyl, 5-pyrimidinyl, 5-tetrazolyl, pyrazolyl, pyrazinyl or 1,3,5-triazinyl.

Even more preferably, T or $R^7$ is 3-1H-benzimidazol-2-one, 3-(1-alkyl)-benzimidazol-2-one, $^2$-pyrazolinyl, 1,3-dihydro-imidazol-2-one, 2-imidazolyl, 2-pyrrolyl, 2-pyrimidinyl, 5-pyrimidinyl, 5-tetrazolyl or pyrazinyl.

Most preferred is when T or $R^7$ is selected from:

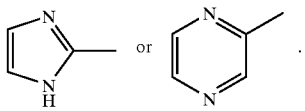

Preferred substituents on T or $R^7$ in the above embodiments are halogen, —$CF_3$, —$OCF_3$, oxo, —COOR' or —CON(R')$_2$, wherein R' is as defined above.

In another preferred embodiment of the present invention, $R^1$ is —$CH_2$—CH($CH_3$)—$CH_3$, —C($CH_3$)$_3$, —CH($CH_3$)$_2$, —CH($CH_3$)—$CH_2$—$CH_3$ or cyclohexyl. Most preferably $R^1$ is cyclohexyl.

According to another preferred embodiment, $R_3$ is selected from —C($CH_3$)$_2$, —CH($CH_3$)$_2$, —CH($CH_3$)—$CH_2$—$CH_3$ or cyclohexyl. More preferably, $R_3$ is selected from —C($CH_3$)$_3$, or —CH($CH_3$)$_2$.

According to yet another preferred embodiment, each $R_2$ is independently selected from —$CH_3$ or hydrogen. Even more preferred is when $R_2$ is hydrogen.

According to another preferred embodiment, $R_5$ is —$CH_2CH_2CH_3$, —$CH_2CH_2CH_2CH_3$, —$CH_2CH_2CH_2F$, —$CH_2CH_2CHF_2$, or —$CH_2CH_2CF_3$. More preferred is when $R_5$ is —$CH_2CH_2CH_2CH_3$ or —$CH_2CH_2CHF_2$. Most preferably $R_5$ is —$CH_2CH_2CH_2CH_3$.

According to another preferred embodiment, $R_5$ is —$CH_2CH_3$, —$CH_2CH_2CH_3$, —$CH_2CH_2F$, —$CH_2CHF_2$, or —$CH_2CF_3$. Most preferred is when $R_5$ is —$CH_2CH_2CH_3$, or —$CH_2CHF_2$. Most preferably $R_5$ is —$CH_2CH_2CH_3$.

According to a preferred embodiment, W is —C(O)—C(O)—$R_6$. Preferably, $R_6$ is isopropyl.

According to another preferred embodiment, W is —C(O)—C(O)—$OR_6$. Preferably, $R_6$ is hydrogen, (C1–C12)-aliphatic, (C6–C10)-aryl, (C3–C10)-cycloalkyl or -cycloalkenyl, (C3–C10)-heterocyclyl or ($C_5$–$C_{10}$) heteroaryl. More preferably, $R_6$ is H or methyl.

According to another preferred embodiment, W is —C(O)—C(O)—N($R_6$)$_2$. Preferably, $R_6$ is hydrogen, (C3–C10)-cycloalkyl or -cycloalkenyl, or (C3–C10)-heterocyclyl.

In another preferred embodiment of formula I is where W is C(O)—C(O)—N($R_6$)$_2$, the $NR_6R_6$ portion of the W moiety is —NH— (C3–C6)cycloalkyl, —NH—CH($CH_3$)—(C6–C10)aryl or —NH—CH($CH_3$)—(C3–C10) heterocyclyl, or —NH—CH($CH_3$)—($C_5$–$C_{10}$)heteroaryl, wherein said aryl, heterocyclyl, or heteroaryl is optionally substituted with halogen.

Alternatively, the $NR_6R_6$ portion is —NH—($C_3$–$C_6$) cycloalkyl, —NH—CH($CH_3$)—(C6–C10)aryl, or —NH—CH($CH_3$)—(C5–C10)heteroaryl, wherein said aryl or said heterocyclyl is optionally substituted with halogen; or $NR_6R_6$ is —NH—(C3–C6) cycloalkyl, —NH—CH($CH_3$)—(C6–C10)aryl, or —NH—CH($CH_3$)—(C3–C10) heterocyclyl, wherein said aryl or said heterocyclyl is optionally substituted with halogen.

In other preferred embodiment of formula I, $NR_6R_6$ in W is:

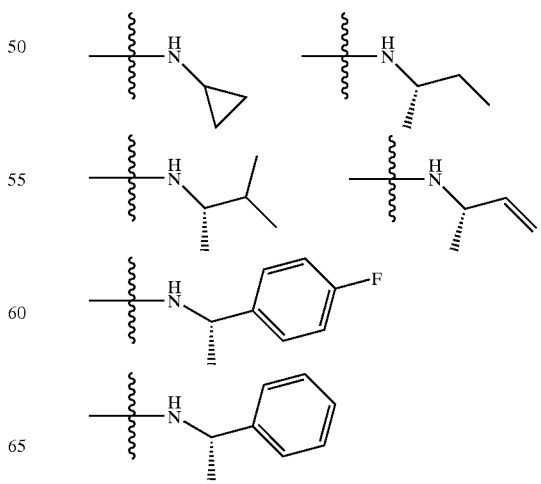

-continued

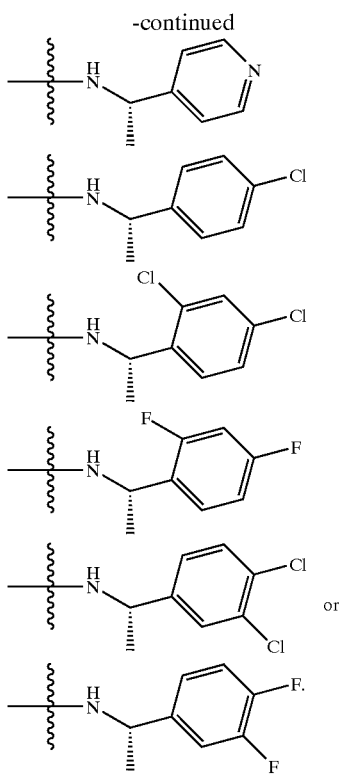

More preferably, NR$_6$R$_6$ is:

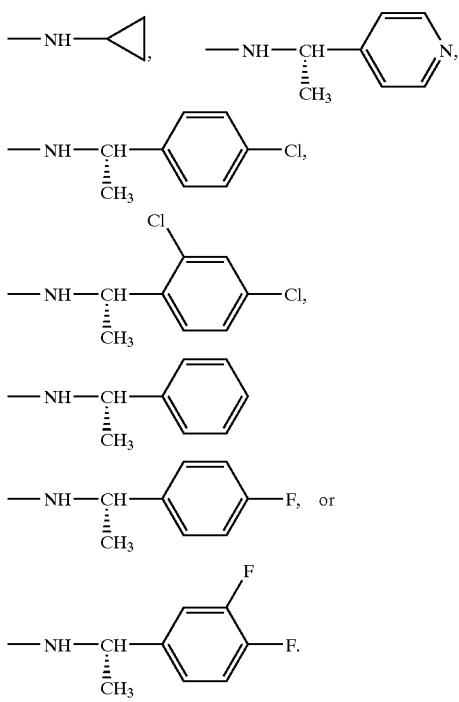

Even more preferably, NR$_6$R$_6$ is:

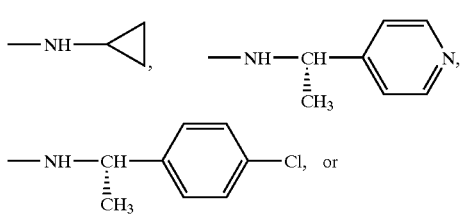

-continued

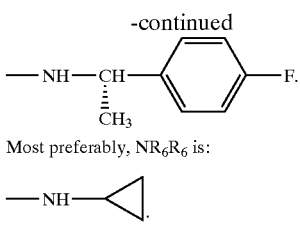

Most preferably, NR$_6$R$_6$ is:

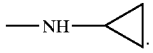

In a preferred embodiment of the present invention, X is —[CH$_2$]$_o$—, —[CJ'J']$_o$—, —[CH$_2$]$_m$—O—, —[CH$_2$]$_m$—S(O)$_2$—, —[CH$_2$]$_m$—SO—, —[CR$_{20}$R$_{20}$]$_m$—NR$_{21}$—, or —[CR$_{20}$R$_{20}$]$_m$—NJ"—.

In a more preferred embodiment of the present invention, X is —CR$_{20}$R$_{20}$—; —O—; —S(O)$_2$; or NR$_{21}$.

Preferred embodiments of R$_{20}$ are selected from hydrogen, —C$_1$-C$_6$-aliphatic and —O—(C$_1$-C$_6$-aliphatic); or each R$_{20}$ is taken together with the carbon atoms to which they are bound to form a (C3–C6)cycloalkyl. Preferably, these aliphatic groups are alkyl groups.

Preferred embodiments of R$_{21}$ are selected from hydrogen and —C(O)—O—R$_{22}$.

In yet another preferred embodiment m in X is 0.

In yet another preferred embodiment, X is —CH$_2$—, —O—, —SO$_2$— or —NR$_{21}$—, wherein R$_{21}$ is hydrogen.

More preferably, X is —CH$_2$—.

Even more preferred is when the bridged bicyclic moiety is fully saturated.

According to another preferred embodiment of this invention, T contains at least one hydrogen bond donor moiety selected from —NH$_2$, —NH—, —OH, and —SH.

In a preferred embodiment, T is:

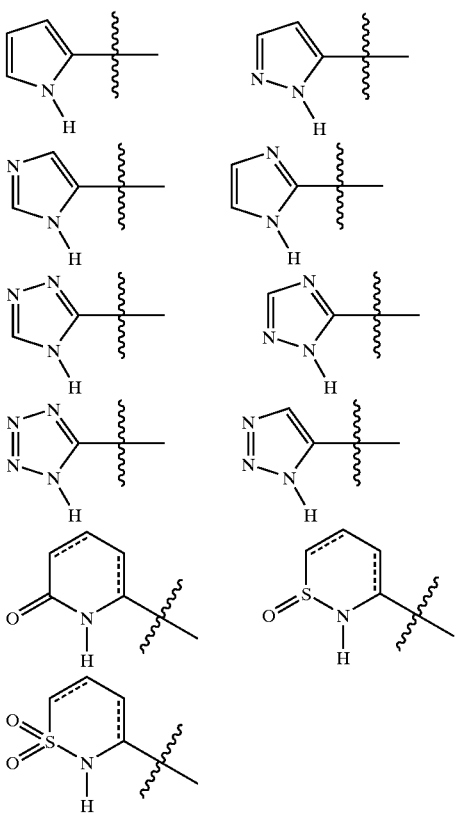

-continued
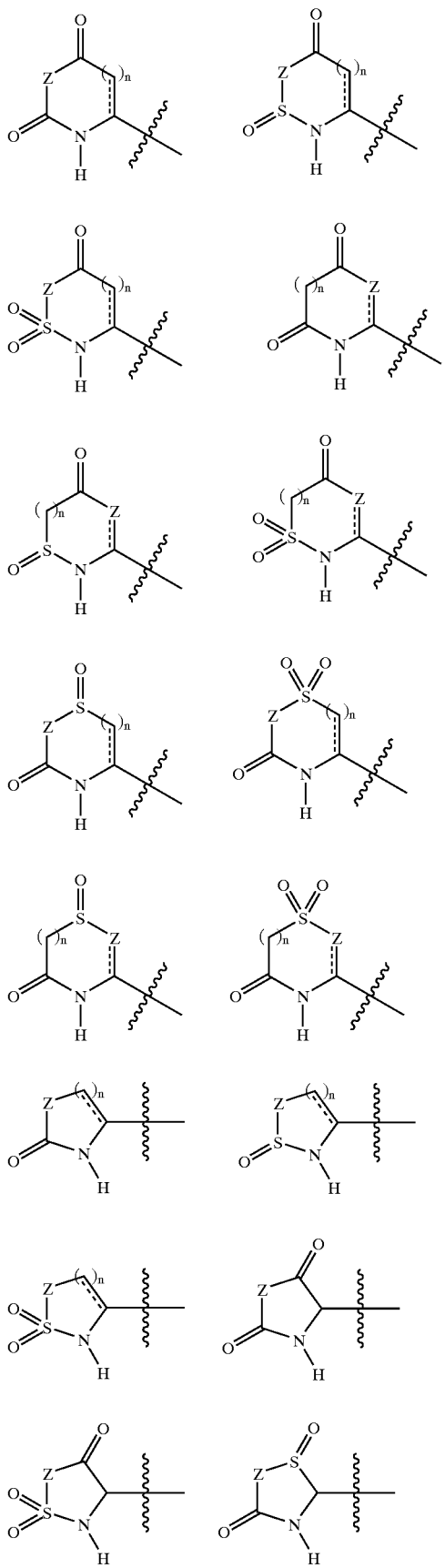
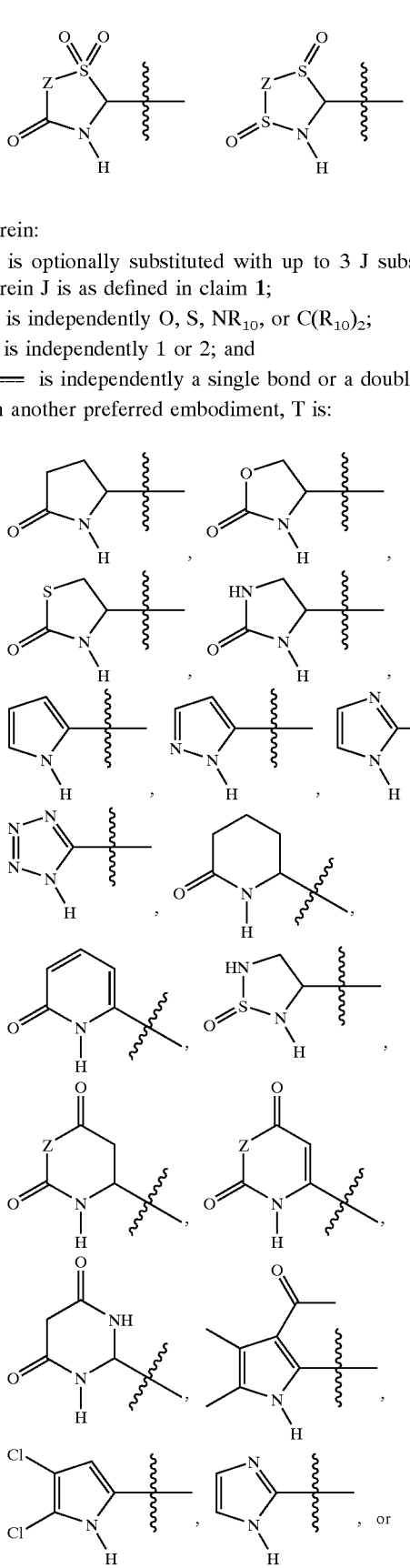
wherein:
T is optionally substituted with up to 3 J substituents, wherein J is as defined in claim 1;
Z is independently O, S, $NR_{10}$, or $C(R_{10})_2$;
n is independently 1 or 2; and
═══ is independently a single bond or a double bond.
In another preferred embodiment, T is:
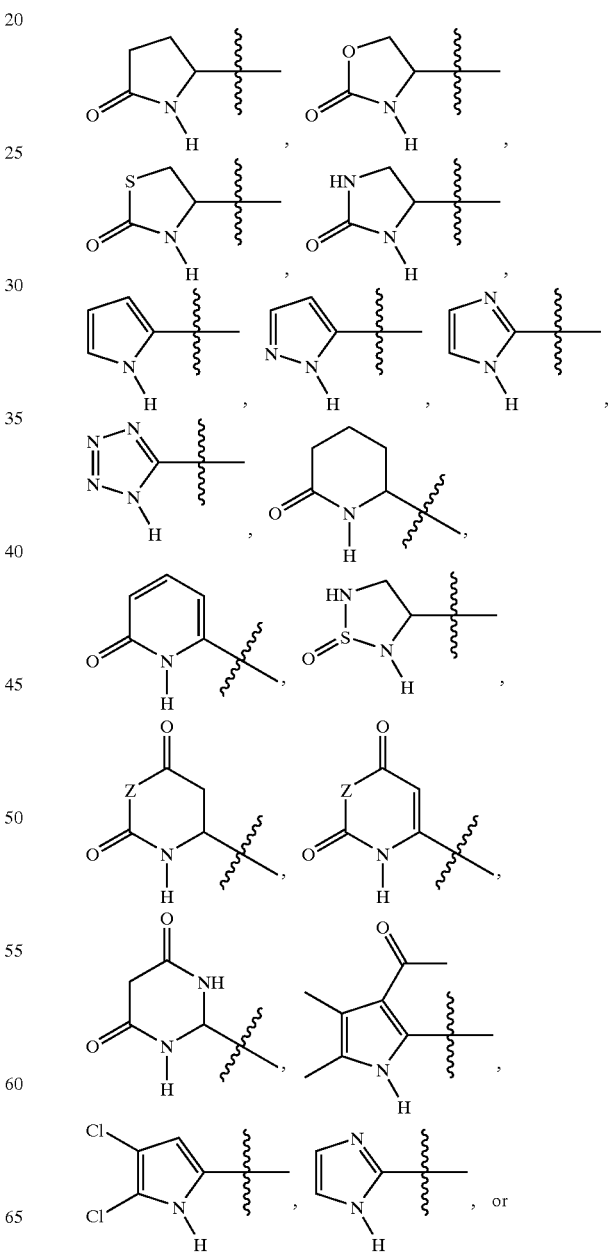

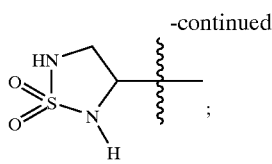

wherein Z is as defined above.

More preferably T is

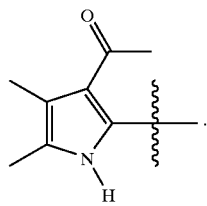

According to another preferred embodiment, T is:

(C6–C10)-aryl, (C6–C10)-aryl-(C1–C12)aliphatic, (C3–C10)-cycloalkyl or -cycloalkenyl,

[(C3–C10)-cycloalkyl or -cycloalkenyl]-(C1–C12)-aliphatic, (C3–C10)-heterocyclyl, (C3–C10)-heterocyclyl-(C1–C12)-aliphatic, (C5–C10)heteroaryl, or (C5–C10)heteroaryl-(C1–C12)-aliphatic, wherein each T is optionally substituted with up to 3 J substituents.

According to yet another preferred embodiment of this invention, T:

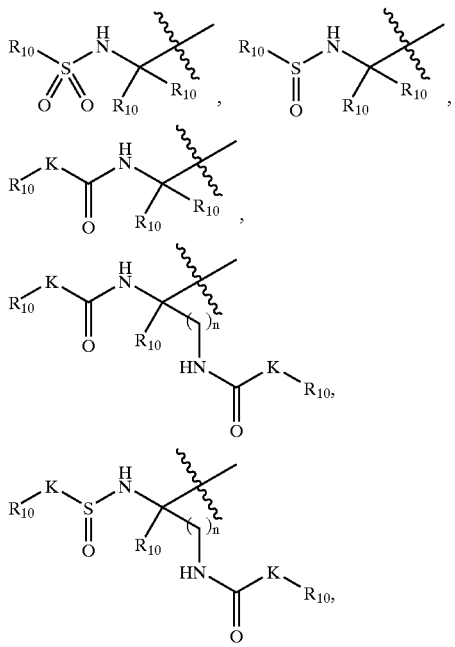

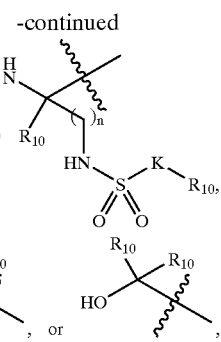

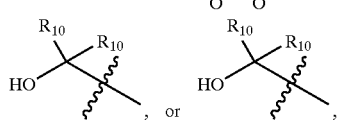

wherein:

$R_{10}$ is:

hydrogen, (C1–C12)-aliphatic, (C6–C10)-aryl, (C6–C10)-aryl-(C1–C12)aliphatic, (C3–C10)-cycloalkyl or -cycloalkenyl,

[(C3–C10)-cycloalkyl or -cycloalkenyl]-($C_1$–C12)-aliphatic, (C3–C10)-heterocyclyl, (C3–C10)-heterocyclyl-(C1–C12)-aliphatic, (C5–C10)heteroaryl, or (C5–C10)heteroaryl-(C1–C12)-aliphatic, wherein each T is optionally substituted with up to 3 J substituents;

K is a bond, —O—, —S—, —$NR_9$—, —C(O)—, or —C(O)—$NR_9$—, wherein $R_9$ is hydrogen or C1–C12 aliphatic; and n is 1–3.

More preferably, T is:

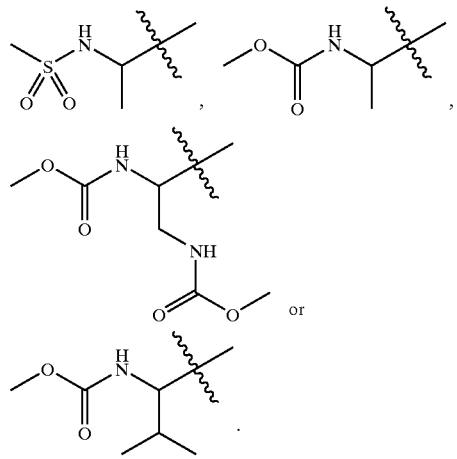

In yet another preferred embodiment, $R_1$ is:

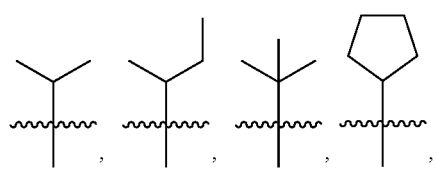

-continued

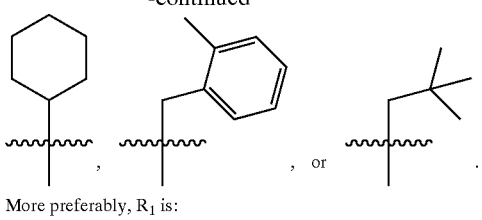

More preferably, R₁ is:

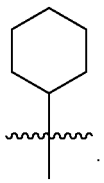

In yet another preferred embodiment, R₃ is:

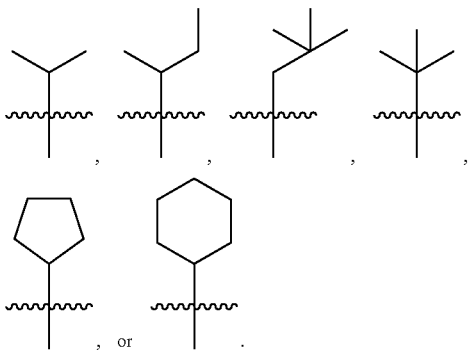

More preferably, R₃ is:

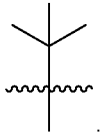

In yet another preferred embodiment, R₅ is:

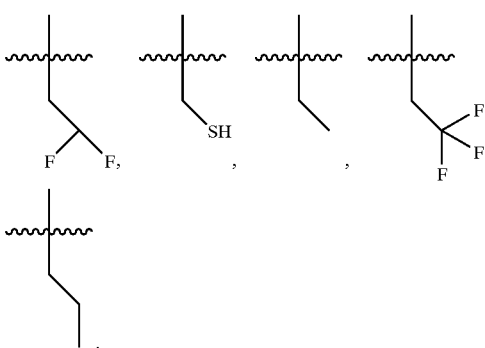

More preferably, R₅ is:

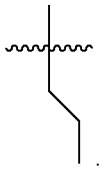

In yet another preferred embodiment, $R_2$ and $R_4$ are each independently H, methyl, ethyl, or propyl.

More preferably, $R_2$ and $R_4$ are each H.

According to a preferred embodiment, V is —C(O)—$NR_8$—. More preferably, V is —C(O)—NH—.

More preferably, the compound of this invention has the structure and stereochemistry depicted below in formula II:

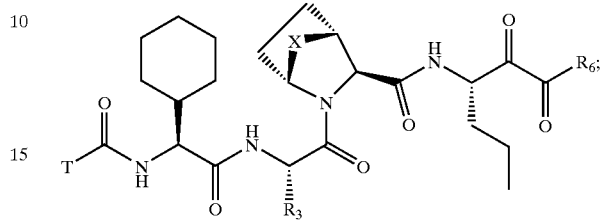

wherein $R_3$ and $R_6$ represent the most preferred embodiments set forth above.

Any of the preferred embodiments recited above may be combined to produce a preferred embodiment of this invention.

The compounds of this invention may be synthesized by standard chemical schemes well-known in the art. Such schemes are set forth below, but other equivalent schemes, which will be readily apparent to the ordinary skilled organic chemist, may alternatively be used to synthesize various portions of the molecule. For example, compounds of formula I, wherein W is C(O)OH or C(O)C(O))$R_6$ may be prepared according to the methods depicted in schemes 11 and/or 12. More specific synthesis schemes for individual compounds within applicants' invention are set forth in the examples.

Scheme 1.
Synthesis of the Azabicyclo [2.2.1] heptane-3-carboxylic acid
when o = 1, m = 0, each $R_{20}$ = H, and $R_3$ = t-Bu

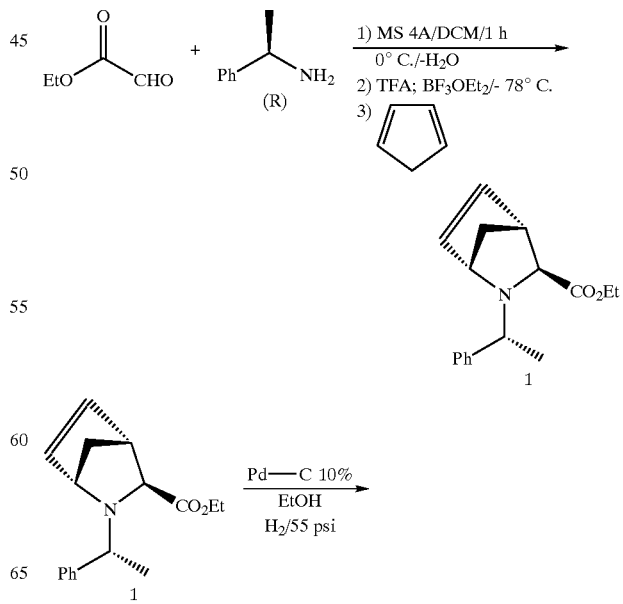

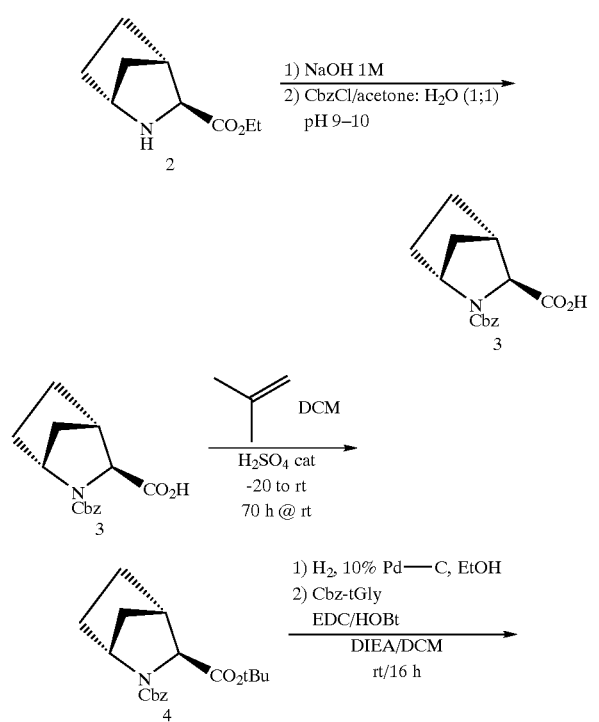
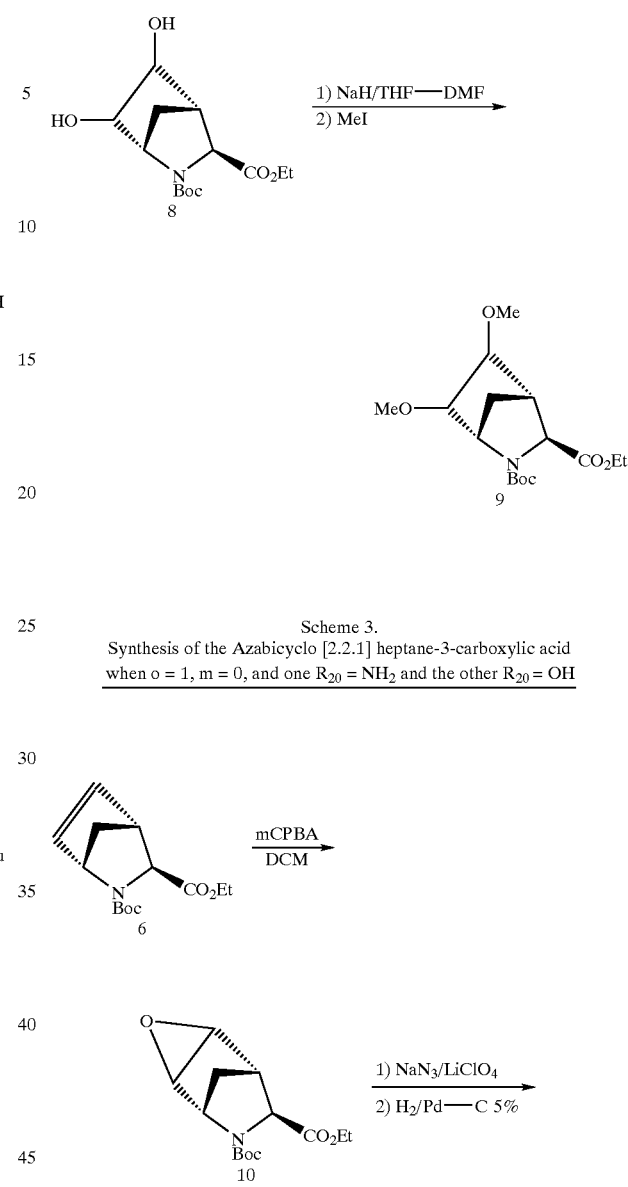
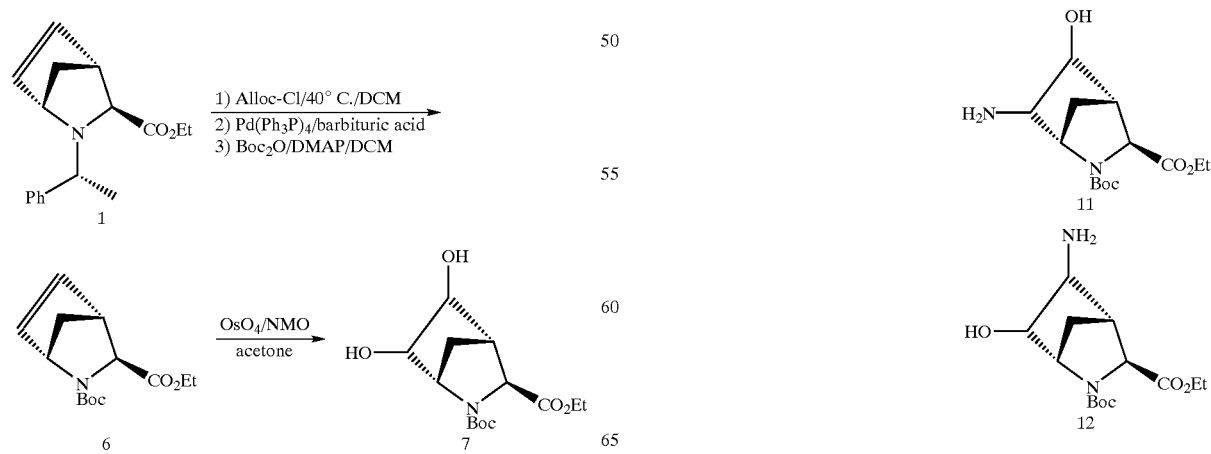
Scheme 2.
Synthesis of the Azabicyclo [2.2.1] heptane-3-carboxylic acid when o = 1, m = 0, each $R_{20}$ = OMe
Scheme 3.
Synthesis of the Azabicyclo [2.2.1] heptane-3-carboxylic acid when o = 1, m = 0, and one $R_{20}$ = $NH_2$ and the other $R_{20}$ = OH Scheme 4.
Synthesis of the Azabicyclo [2.2.1] heptane-3-carboxylic acid
when o = 1, m = 0, and one $R_{20}$ = Me and the other $R_{20}$ = OH
Scheme 5.
Synthesis of the Azabicyclo [2.2.1] heptane-3-carboxylic acid
when o = 1, m = 0, and one $R_{20}$ = Me and the other $R_{20}$ = H
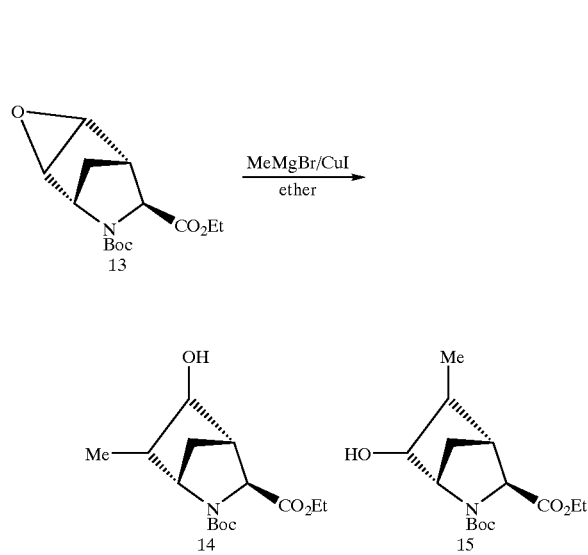
Scheme 6.
Synthesis of the Azabicyclo [2.2.2] octane-3-carboxylic acid
when o = 2, m = 0, each $R_{20}$ = H, and $R_3$ = t-Bu
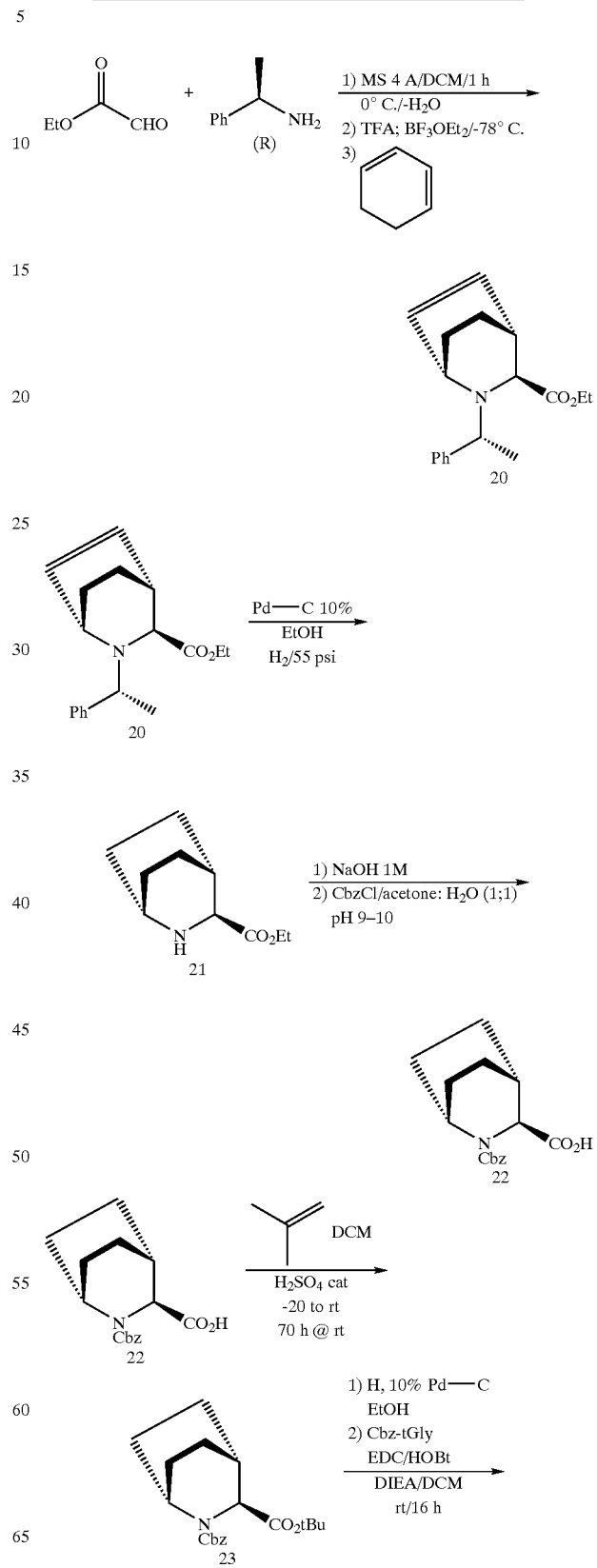

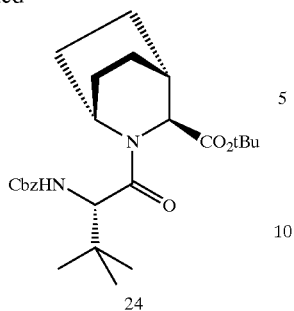
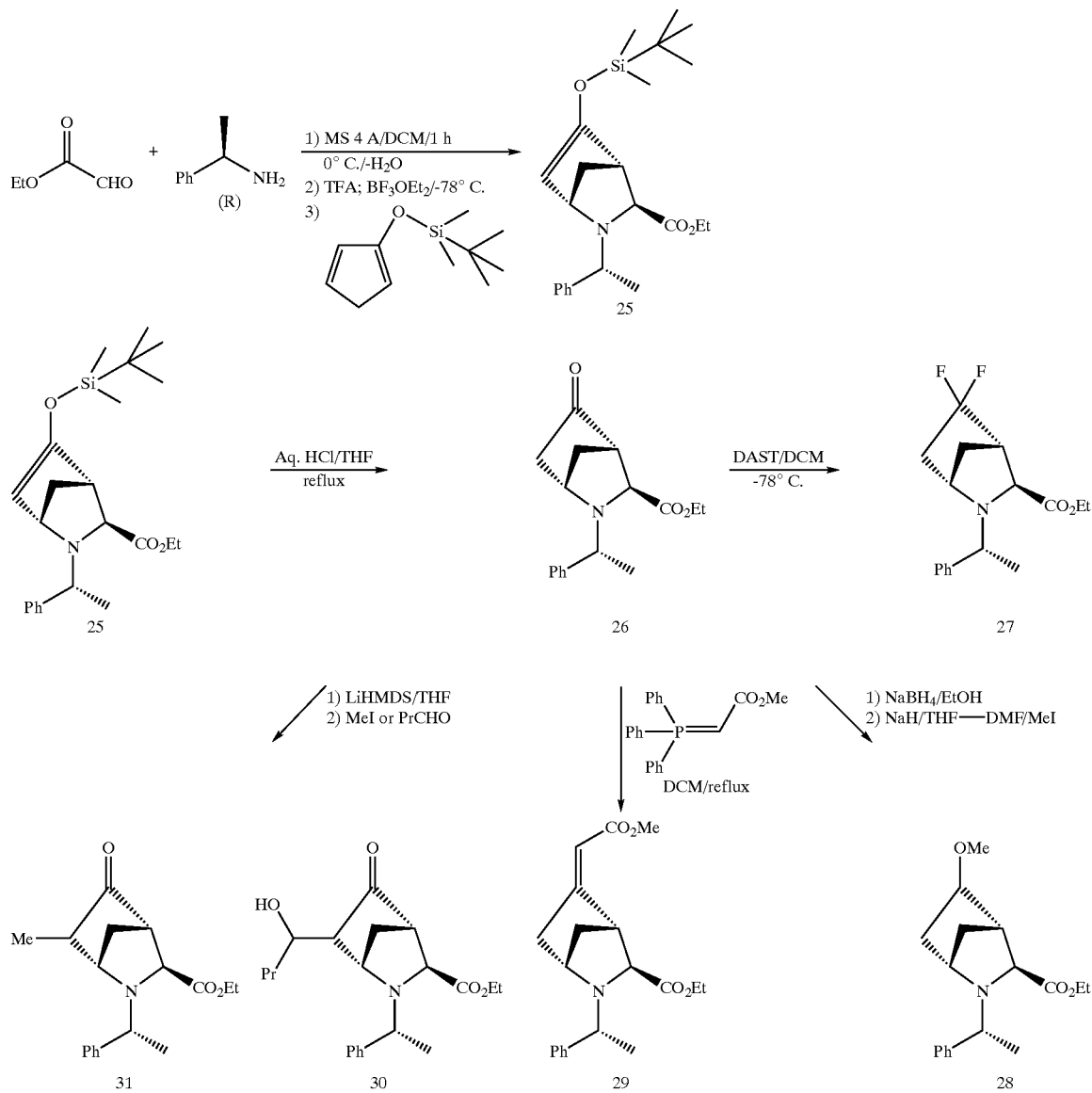
Scheme 7.
Synthesis of the Azabicyclo [2.2.1] heptane-3-carboxylic acid
when o = 1, m = 0, and each $R_{20}$ = H Scheme 8.
Synthesis of Scaffolds when x is o
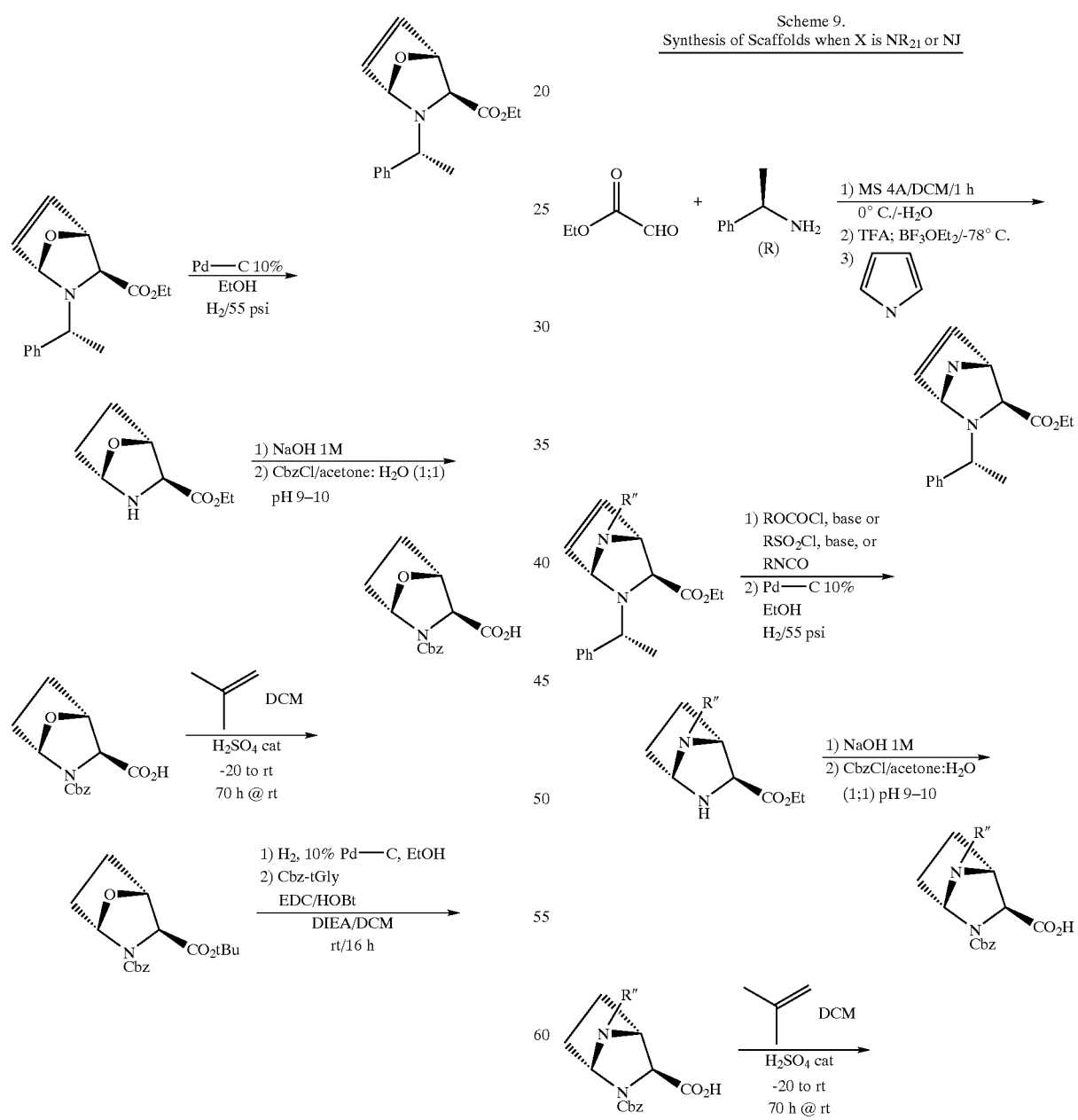
Scheme 9.
Synthesis of Scaffolds when X is $NR_{21}$ or NJ

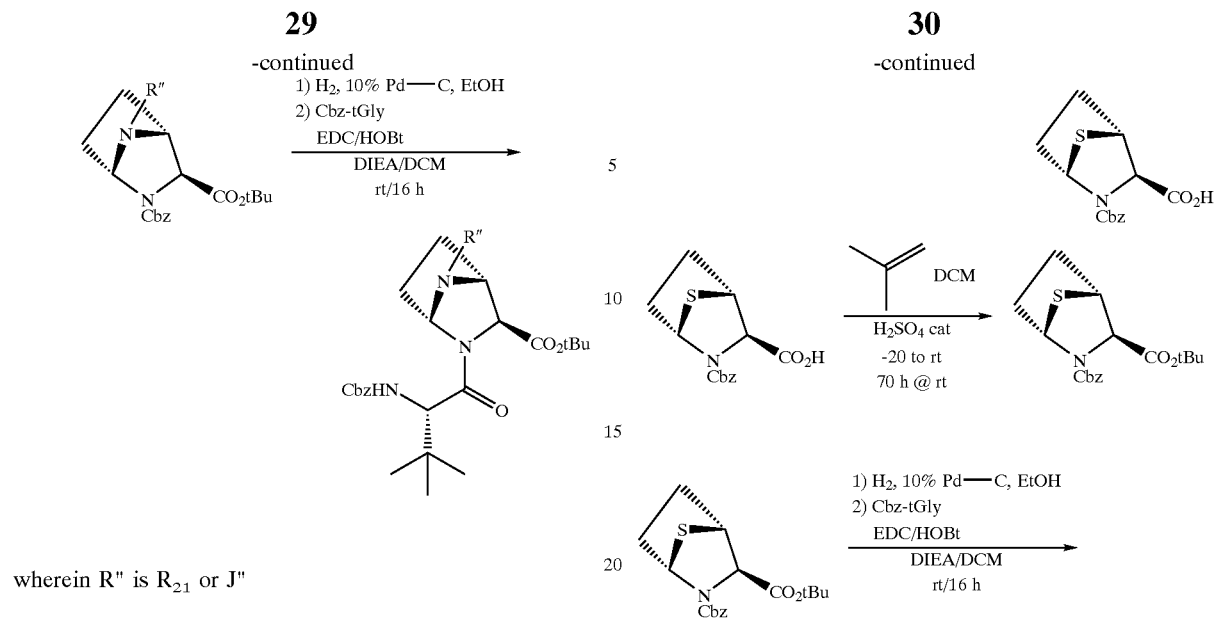
wherein R″ is R₂₁ or J″
Scheme 10.
Synthesis of Scaffolds when X is SO or SO₂
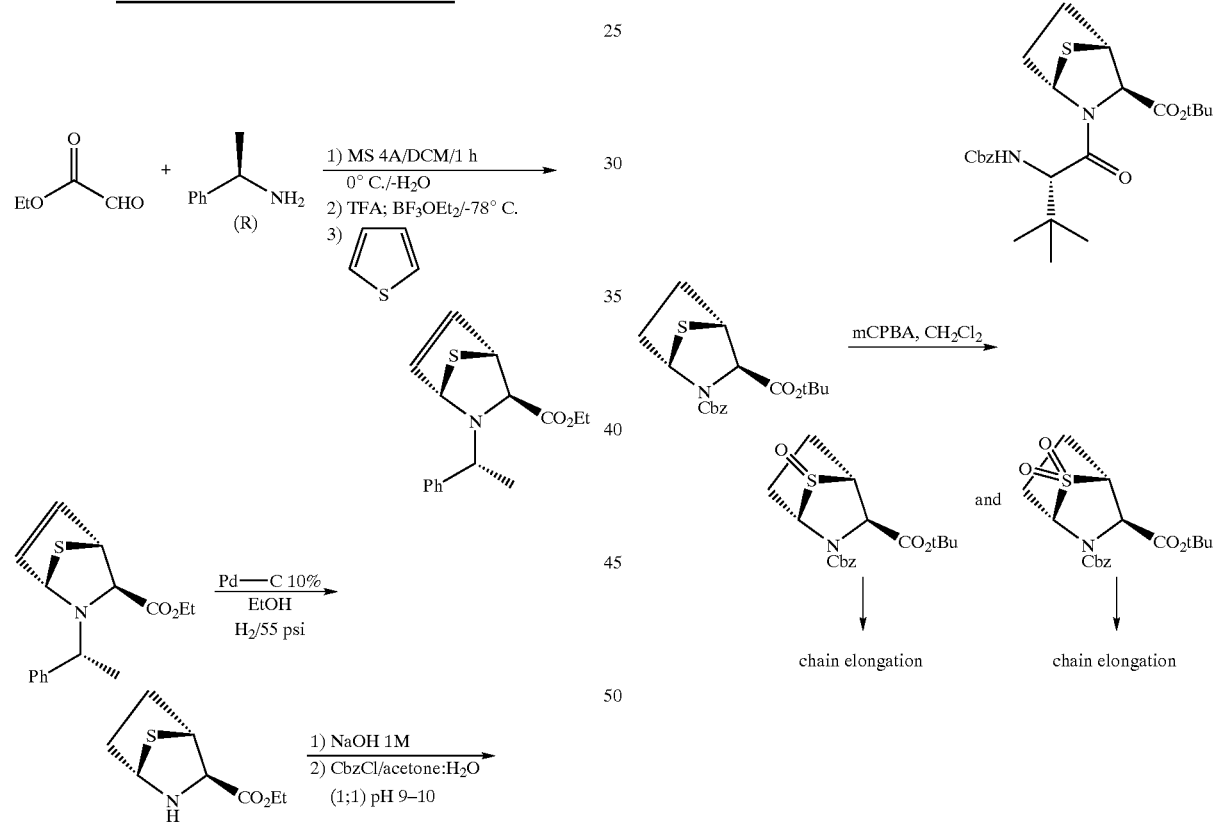
Scheme 11.
Synthesis of Compounds of Formula I when W is
C(O)C(O)N(R₆)₂—
Method A

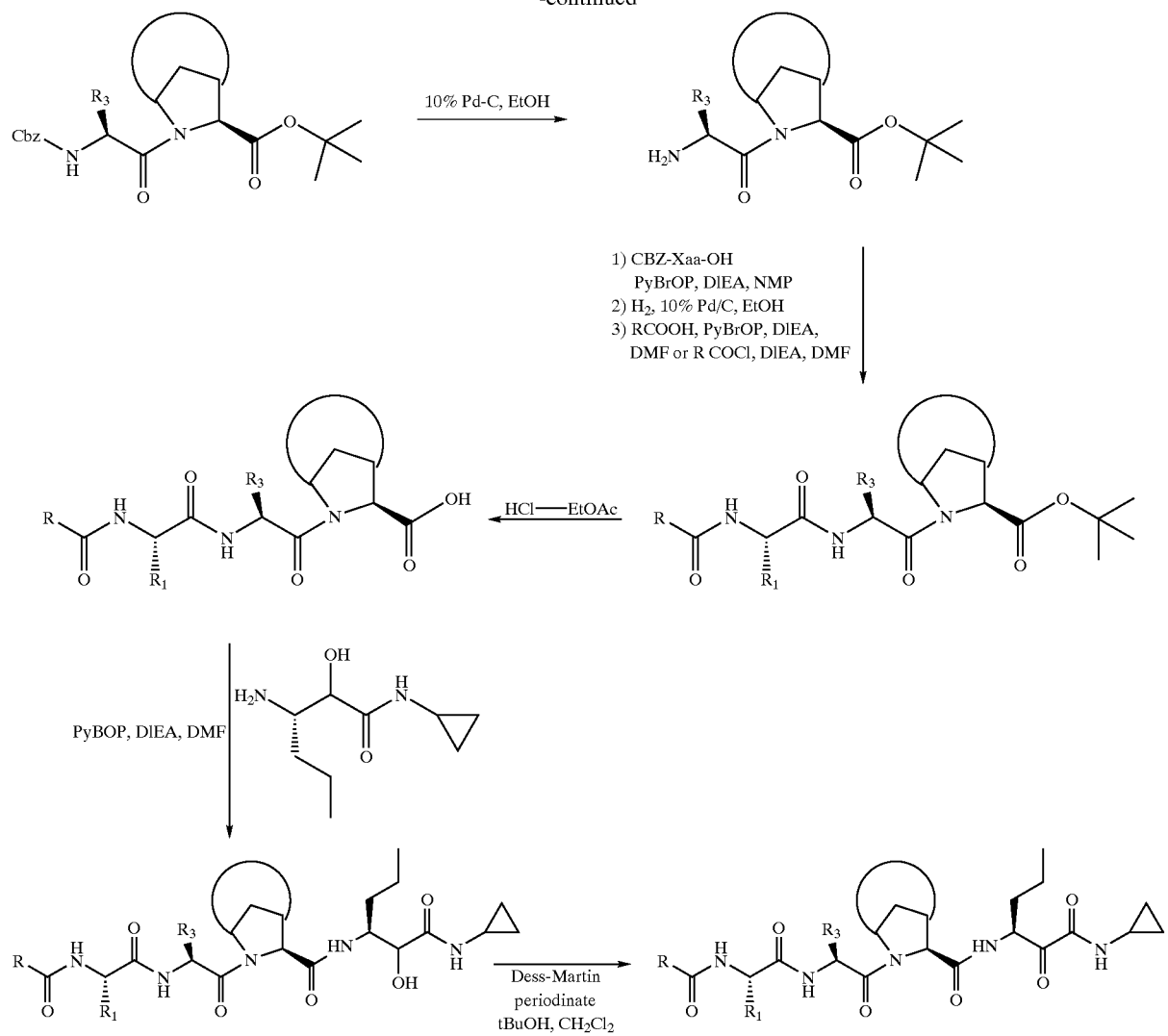
wherein RC(O)NH— corresponds to T-V-
Scheme 12.
Synthesis of Compounds of Formula I when W is
C(O)C(O)N(R_6)_2—
Method B
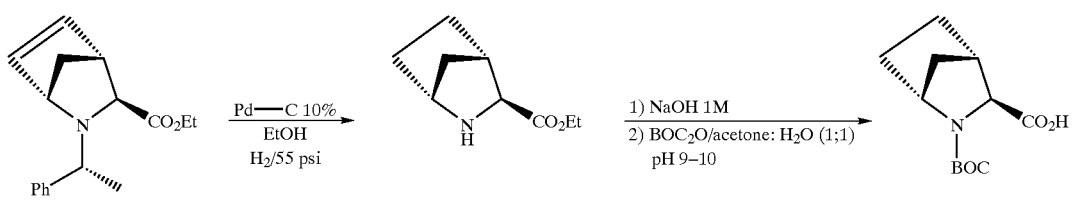

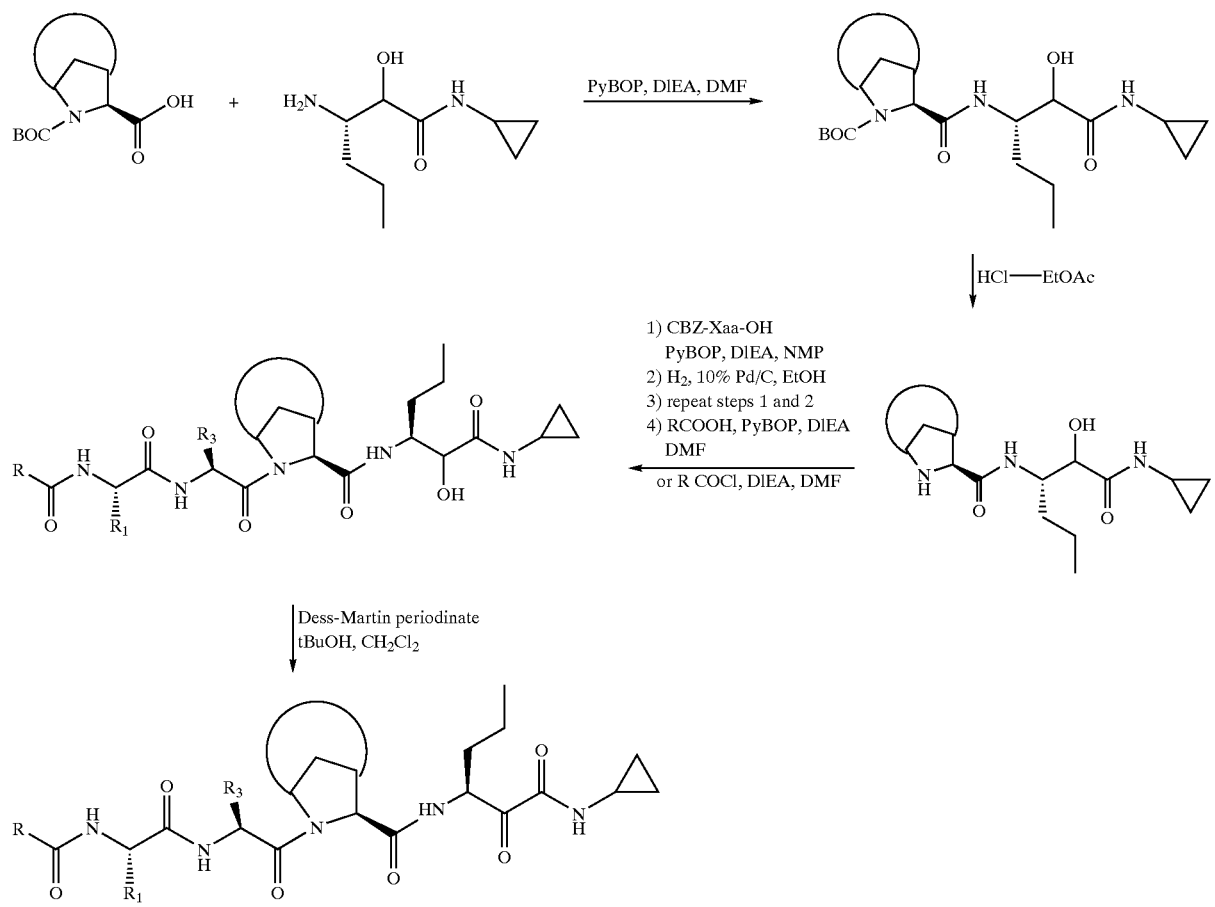
wherein RC(O)NH— corresponds to T-V-
Scheme 13.
Synthesis of Compounds of Formula I when W is
C(O)C(O)R$_6$——
Method A
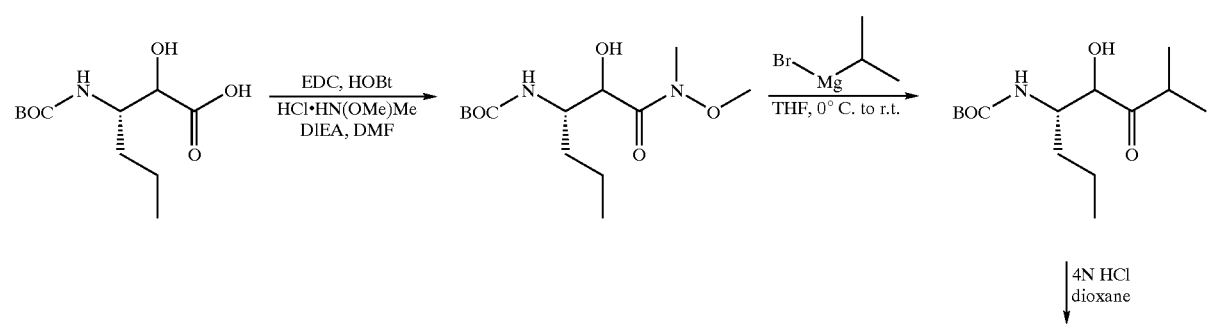

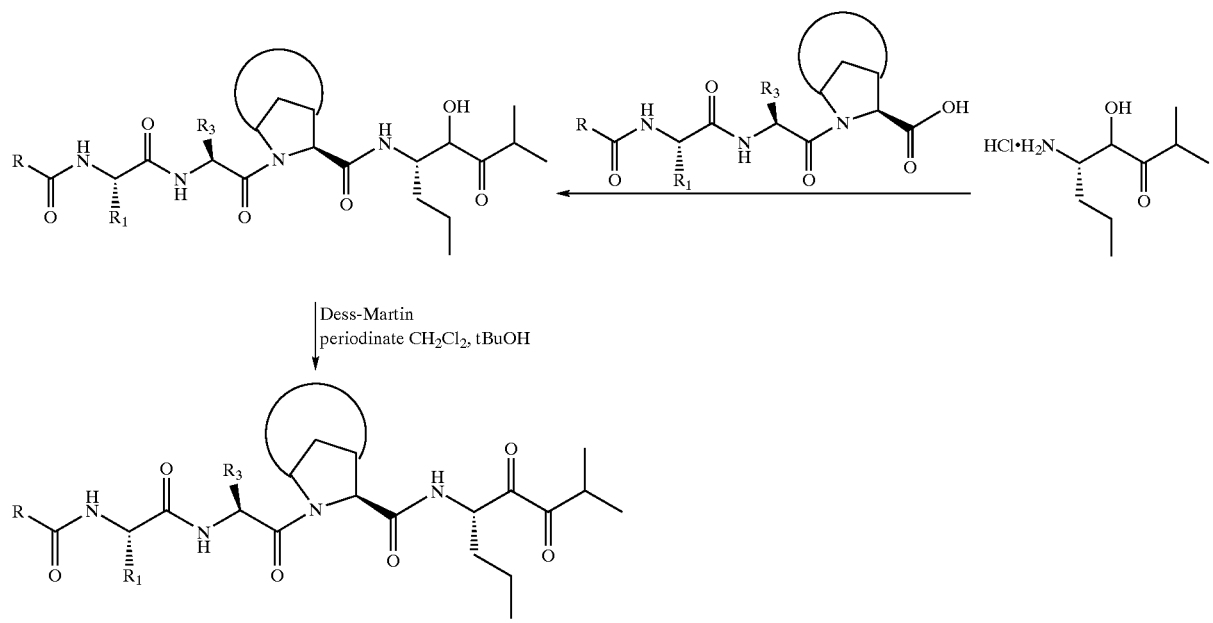
wherein RC(O)NH— corresponds to T-V-
Scheme 14.
Synthesis of Compounds of Formula I when W is
C(O)C(O)R$_6$—
Method B
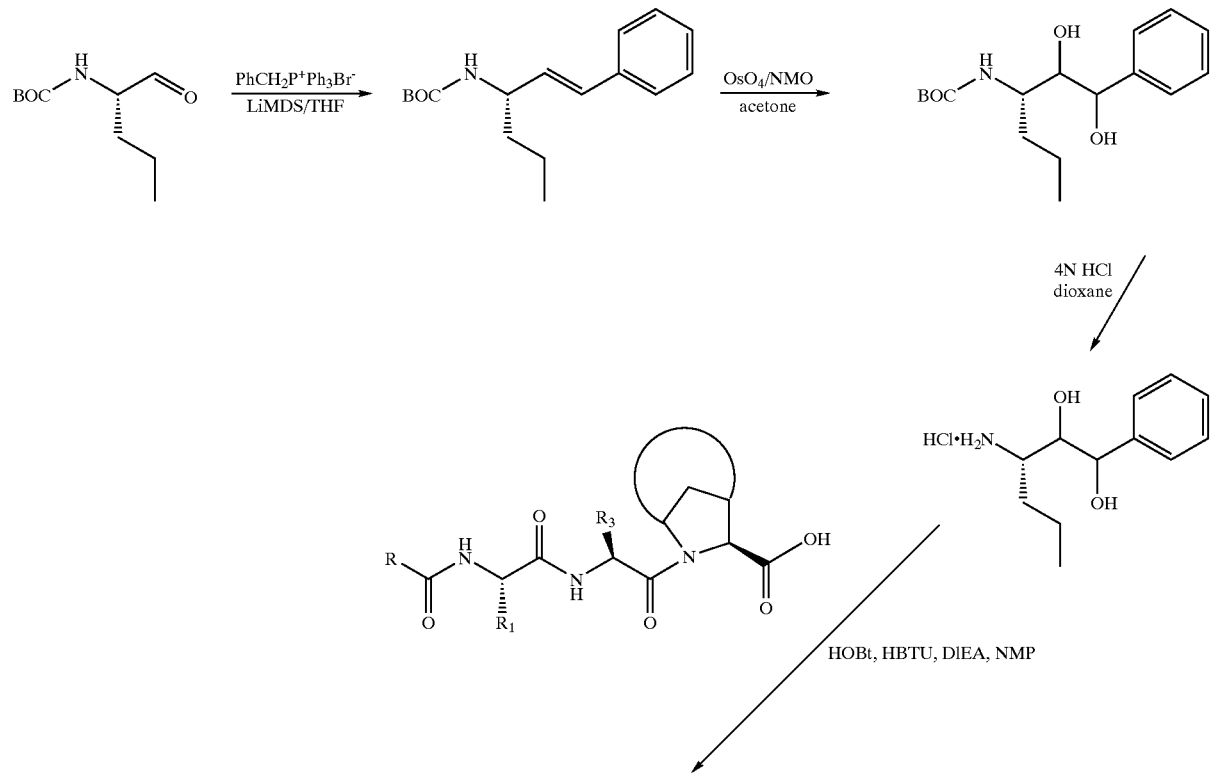

-continued

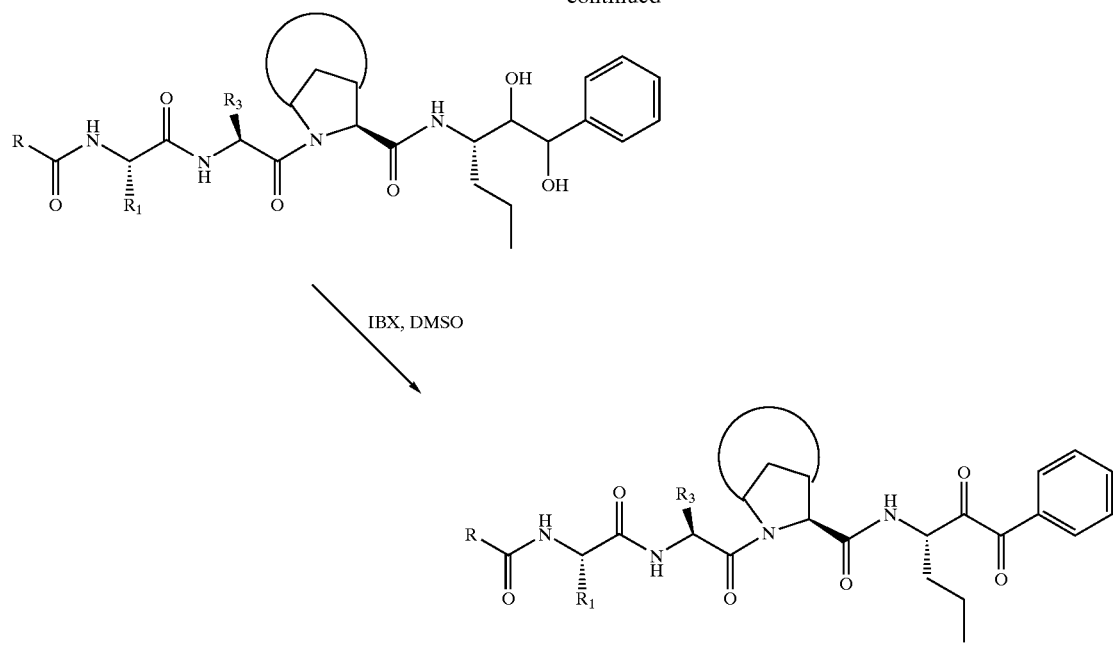

wherein RC(O)NH— corresponds to T-V-

As set forth above, the compounds of this invention are capable of inhibiting the activity of HCV NS3-NS4A protease. In order to quantitate the activity of the compounds of this invention, cells containing HCV replicon were incubated with the compounds of this invention, and a Taqman Real Time PCR assay was conducted to determine the percentage inhibition of HCV RNA level and the IC50 were calculated therefrom. The result are shown below in Table 1:

TABLE 1

| Cmpd No. | Structure | Ki (nM) | IC50 (nM) |
|---|---|---|---|
| 1 | 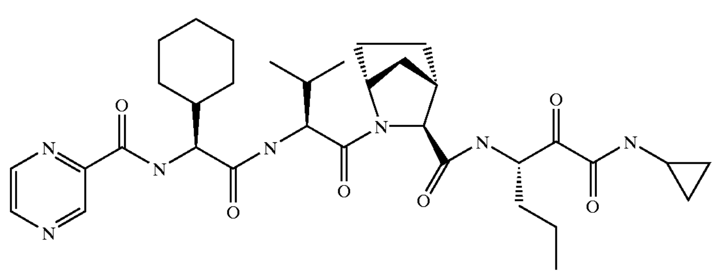 | 220 | >1000 |
| 2 | 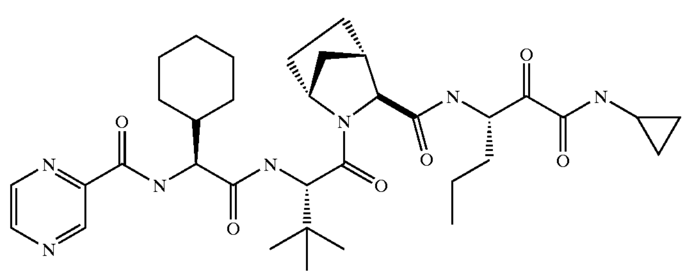 | 90 | 886 |

TABLE 1-continued

| Cmpd No. | Structure | Ki (nM) | IC50 (nM) |
|---|---|---|---|
| 3 | 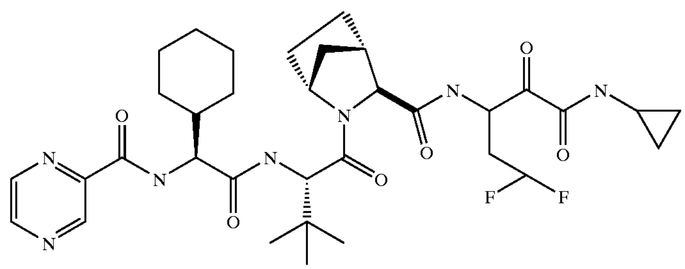 | 63 | 632 |
| 4 | 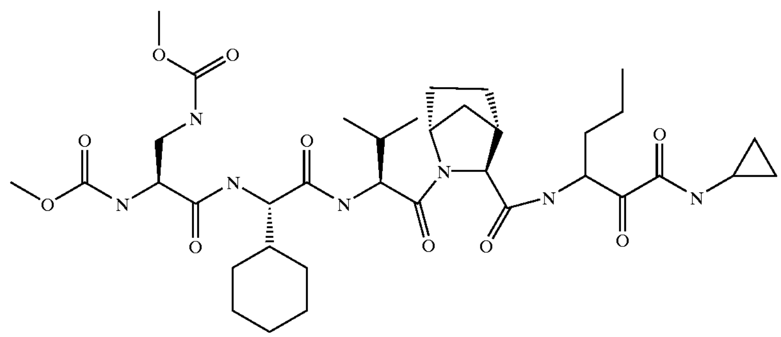 | 95 | >10000 |
| 5 | 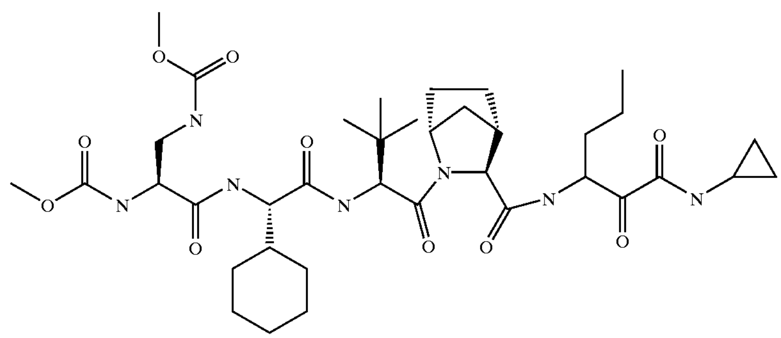 | 39 | 1410 |
| 6 | 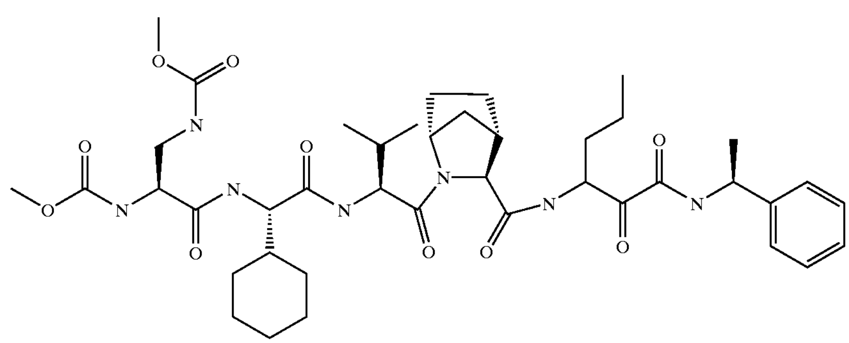 | 96 | 2650 |

TABLE 1-continued

| Cmpd No. | Structure | Ki (nM) | IC50 (nM) |
|---|---|---|---|
| 7 | 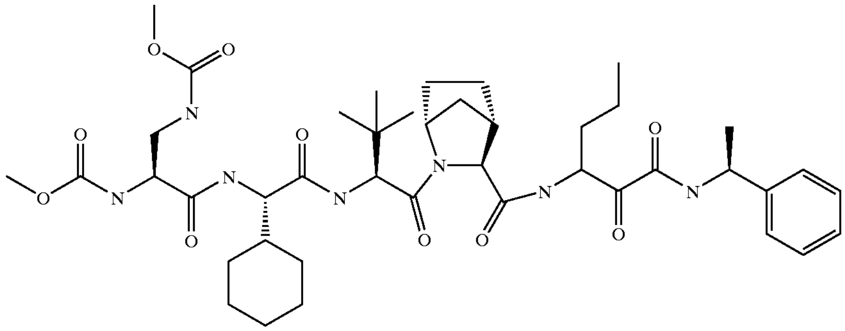 | 49 | 449 |
| 8 | 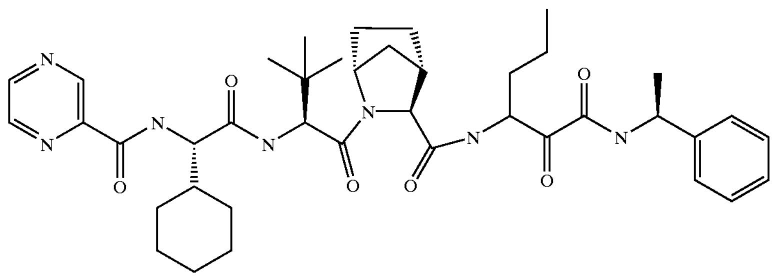 | 110 | 679 |
| 9 | 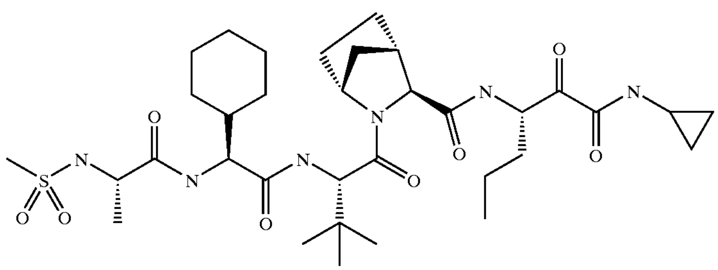 | 55 | 4310 |
| 10 | 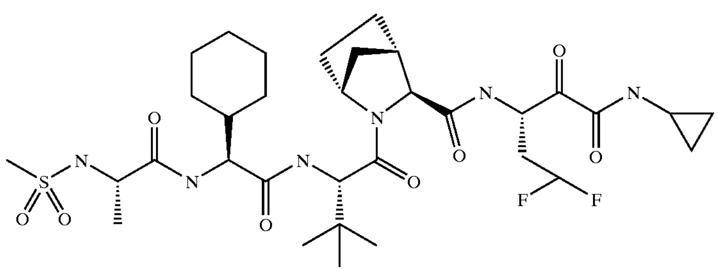 | 28 | 10000 |
| 11 | 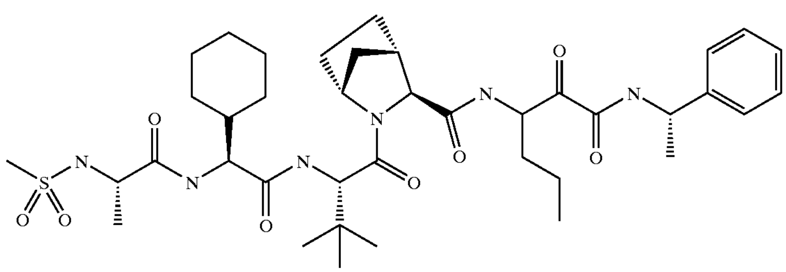 | 50 | 1230 |

TABLE 1-continued

| Cmpd No. | Structure | Ki (nM) | IC50 (nM) |
|---|---|---|---|
| 12 | 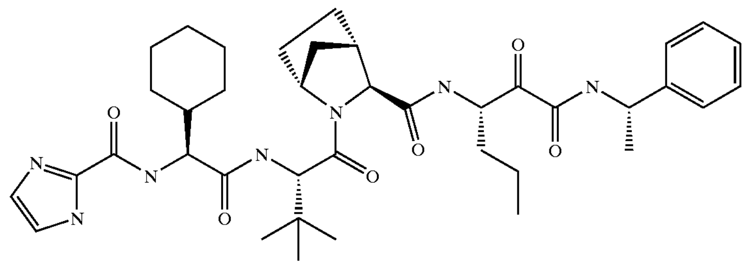 | 68 | 412 |
| 13 | 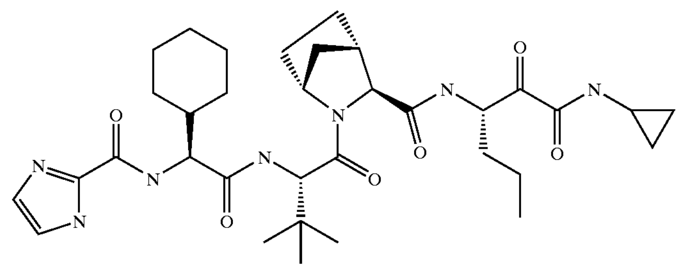 | 42 | 251 |
| 14 | 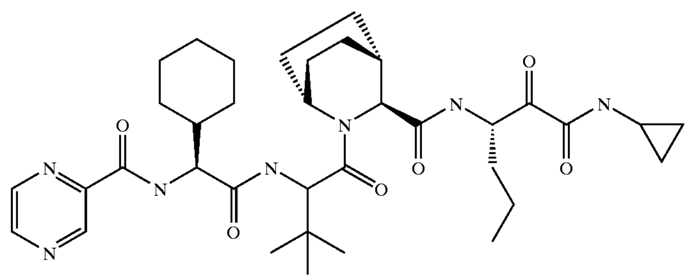 | 125 | 1240 |
| 15 | 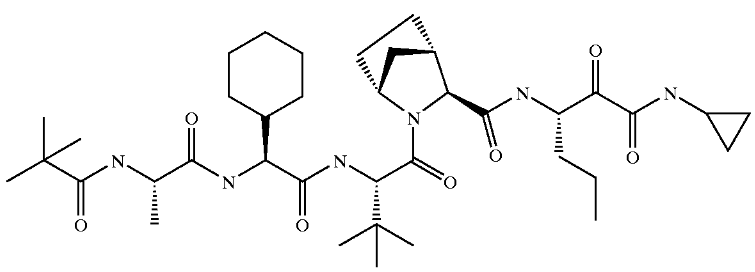 | 66 | 1295 |
| 16 | 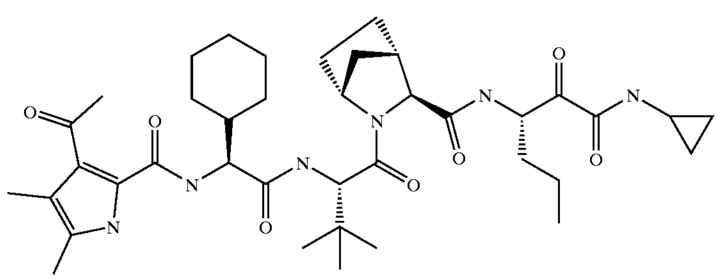 | 54 | <100 |

| Cmpd No. | Structure | Ki (nM) | IC50 (nM) |
|---|---|---|---|
| 17 | 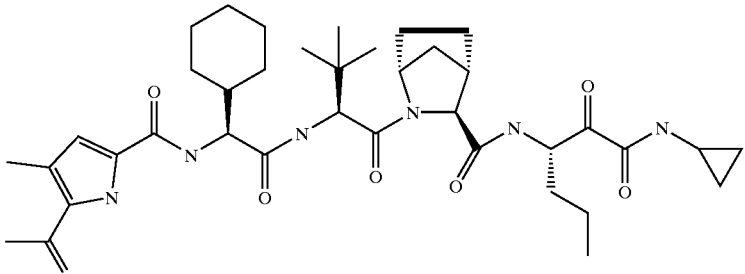 | | |
| 18 | 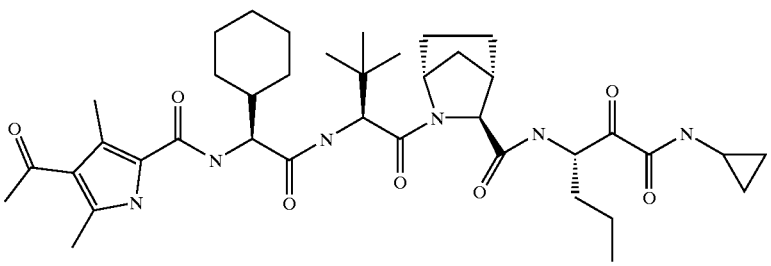 | | |

Another embodiment of this invention provides a composition comprising a compound of formula I or a pharmaceutically acceptable salt thereof in an amount effective to decrease the viral load in a sample or in a patient, wherein said virus encodes a serine protease necessary for the viral life cycle, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferred are pharmaceutical compositions formulated for oral administration.

In a related embodiment, the compositions of this invention additionally comprise another anti-viral agent, preferably an anti-HCV agent. Such anti-viral agents include, but are not limited to, immunomodulatory agents, such as $\alpha$-, $\beta$-, and $\gamma$-interferons and pegylated derivatized interferon-$\alpha$ compounds; other anti-viral agents, such as ribavirin and amantadine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. No. 5,807,876, mycophenolic acid and derivatives thereof); or combinations of any of the above.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

According to another embodiment, the invention provides a method for treating a patient infected with a virus characterized by a virally encoded serine protease that is necessary for the life cycle of the virus by administering to said patient a pharmaceutically acceptable composition of this invention. Preferably, the methods of this invention are used to treat a patient suffering from a HCV infection. Such treatment may completely eradicate the viral infection or reduce the severity thereof. More preferably, the patient is a human being.

In an alternate embodiment, the methods of this invention additionally comprise the step of administering to said patient an anti-viral agent preferably an anti-HCV agent. Such anti-viral agents include, but are not limited to, immunomodulatory agents, such as $\alpha$-, $\beta$-, and $\gamma$-interferons and pegylated derivatized interferon-$\alpha$ compounds; other antiviral agents, such as ribavirin and amantadine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. No. 5,807,876, mycophenolic acid and derivatives thereof); or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention. Such materials include, but are not limited to, surgical instruments and garments; laboratory instruments and garments; blood collection apparatuses and materials; and invasive devices, such as shunts, stents, etc.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. Preferably, the viral serine protease isolated by this method is HCV NS3-NS4A protease.

In order that this invention be more fully understood, the following examples are set forth. These examples are for the purpose of illustration only and are not to be construed as limiting the scope of the invention in any way.

EXAMPLE 1

Ethyl(1S,3S,4R)-2-[(1R)-1-phenylethyl]-2-azabicyclo[2.2.1]hept-5-ene-3-carboxylate (1) (Example for n=o, m=0; each $R_{20}$=H) see Scheme 1

(R)-Methylbenzylamine (15 mL; 0.118 mol; 1.05 eq) was added to a stirred 0° C. solution of for example, ethyl glyoxylate 50% in toluene (23 mL; 0.112 mol; 1.0 eq) in 600 mL of anhydrous DCM containing 27 g of 4A molecular sieve. The reaction mixture was stirred at 0° C. for 1 h. then it was lowered to −78° C. The 3 following reagents were sequentially added with 5 min. in between each addition: TFA (9.08 mL; 0.118 mmol; 1.05 eq), boron trifluoride etherate (14.93 mL; 0.118 mol; 1.05 eq) and, for example, cyclopentadiene (16.37 mL; 0.146 mol; 1.3 eq). The reaction mixture was stirred at −78° C. for 5 h before it was allowed to warm to rt. The molecular sieves were separated and the reaction mixture was carefully washed with saturated aqueous sodium hydrogen carbonate (250 mL), brine (250 mL), and dried with magnesium sulfate. Concentration and purification by flash chromatography (Hexanes: EtOAc:TEA (89:10:1) afforded (in order of elution) 2.3 g (7.%) of minor endo-isomer and 23.5 g (78%) of the major exo-isomer 1. The compound was characterized using NMR.

EXAMPLE 2

Ethyl(1S,3S,4R)-2-azabicyclo[2.2.1]heptane-3-carboxylate (2) (Example for o=1, m=0; each $R_{20}$=H)

The aza Diels-Alder adduct 1 (23.5 g; 0.086 mol) was dissolved in 200 mL of absolute ethanol, and, for example, Pd-C 10% (600 mg) was added. The mixture was stirred at rt under hydrogen (55 psi) for 16 h. Filtration through a pad of celite (or nylon/carbon filter combination) and concentration yielded 14.2 g of 2 (97%) as a pale yellow oil which was used directly for the next step. The compound was characterized using NMR.

EXAMPLE 3

(1S,3S,4R)-2-Benzoylazabicyclo[2.2.1]heptane-3-carboxylic Acid 3 (Example for o=1, m=0, each $R_{20}$=H)

Amino ester 2 (3.45 g; 0.0204 mol; 1.0 eq) was added a mixture of, for example, 1N NaOH (71 mL; 0.143 mol; 3.5 eq) and 71 mL of water and stirred at rt for 4 h (TLC monitoring w/mixture of EtOAc and 5% TEA). When the saponification is complete, 100 mL of acetone was added and the temperature was lowered to 0° C. Benzyl chloroformate (3.5 mL; 0.0244 mol; 1.2 eq) in 40 mL of acetone was slowly added and the reaction mixture was allowed to stir at rt for 16 h with maintaining the pH to roughly 9 to 10 with 1N NaOH. The acetone was removed and 200 mL of water was added. The aqueous phase was washed with ether (3×200 mL) and the aqueous phase acidified to pH 2–3 with 2N HCl. Extraction of the product with (3×250 mL) of EtOAc, drying ($Na_2SO_4$) and concentration in vacuo provided 3.85 g (70%) of amino acid 3. The compound was used directly for the next step. The compound was characterized using NMR.

EXAMPLE 4 tert-Butyl(1S,3S,4R)-2-Benzoylazabicyclo[2.2.1]heptane-3-carboxylate (4) (Example for o=1, m=0, each $R_{20}$=H)

In a sealed tube, 140 μL of concentrated sulfuric acid was added to a solution of acid 3 (3.86 g; 0.014 mol) in 30 mL of DCM. The solution was brought to −20° C. and saturated with isobutylene, causing a volume increase of 14 mL. After 70 h at rt, the cap was remove to release the pressure and the solution was added to 25 mL of water containing sodium carbonate sufficient to neutralize all acid. The compound 4 was used directly for the next step without further purification. The compound was characterized using NMR.

Removal of the Cbz group with hydrogenation under 1 atm of hydrogen using Pd-C10% in ethanol gave, after 5 h, the desired aminoester intermediate in quantitative yield.

The crude compound was coupled to tert-butylglycine shown in the next step.

EXAMPLE 5 tert-Butyl Glycine Coupling to Product 5 (Example for 0=1, m=0, each $R_{20}$=H, $R_3$=t-Bu)

To a solution of Cbz-tert-butyl glycine (3.33 g; 0.0126 mol; 1.0 eq) in 20 mL of DCM at 0° C. was added, for example, EDC (2.89 g; 0.015 mol; 1.2 eq), HOBt (2.5 g; 0.0163 mol; 1.3 eq) and DIEA (6.57 mL; 0.038 mol; 3.0 eq). The resulting mixture was stirred at 0° C. for 15 min. after which, the above amino ester was slowly added in 10 mL of DCM. The resulting reaction mixture was stirred at rt for 16 h. Concentrated to a residue that was redissolved in EtOAC. Successive washes with 0.5N HCL, satd' aqueous $NaHCO_3$ and brine gave after drying ($Na_2SO_4$) and concentration in vacuo the desired product which was subjected to flash chromatography (20% EtOAc/80% hexanes) to provide pure 5. The compound was characterized using NMR. The rest of the synthesis was done using standard amino acid coupling which were reported in previous patent.

EXAMPLE 6

Ethyl (1S,3S,4R)-2-[(1R)-1-phenylethyl]-2-azabicyclo[2.2.2]oct-5-ene-3-carboxylate (1) (Example for o=1, m=0; each $R_{20}$=H) see Scheme 2

The preparation of the azabicyclo[2.2.2]oct-5-ene was achieved using the same experimental as above with the procedural change that 1,3-cyclohexadiene was used instead of cyclopentadiene. The rest of the synthesis was done using standard amino acid coupling which have been reported.

EXAMPLE 7

Cells containing hepatitis C virus (HCV) replicon were maintained in DMEM containing 10% fetal bovine serum (FBS), 0.25 mg per ml of G418, with appropriate supplements (media A).

On day 1, replicon cell monolayer was treated with a trypsin:EDTA mixture, removed, and then dilutedh media A into a final concentration of 100,000 cells per ml wit. 10,000 cells in 100 ul are plated into each well of a 96-well tissue culture plate, and culture overnight in a tissue culture incubator at 37° C.

On day 2, compounds (in 100% DMSO) were serially diluted into DMEM containing 2% FBS, 0.5% DMSO, with appropriate supplements (media B). The final concentration of DMSO was maintained at 0.5% throughout the dilution series.

The media on the replicon cell monolayer was removed, and then media B containing various concentrations of compounds was added. Media B without any compound was added to other wells as no compound controls.

Cells were incubated with compound or 0.5% DMSO in media B for 48 hours in a tissue culture incubator at 37° C.

At the end of the 48-hour incubation, the media was removed, and the replicon cell monolayer was washed once with PBS and stored at −80° C. prior to RNA extraction.

Culture plates with treated replicon cell monolayers were thawed, and a fixed amount of another RNA virus, such as Bovine Viral Diarrhea Virus (BVDV) was added to cells in each well. RNA extraction reagents (such as reagents from RNeasy kits) were added to the cells immediately to avoid degradation of RNA. Total RNA was extracted according to the instruction of manufacturer with modification to improve extraction efficiency and consistency. Finally, total cellular RNA, including HCV replicon RNA, was eluted and stored at −80° C. until further processing.

A Taqman real-time RT-PCR quantification assay was set up with two sets of specific primers and probe. One was for HCV and the other was for BVDV. Total RNA extractants from treated HCV replicon cells were added to the PCR reactions for quantification of both HCV and BVDV RNA in the same PCR well. Experimental failure was flagged and rejected based on the level of BVDV RNA in each well. The level of HCV RNA in each well was calculated according to a standard curve that is run in the same PCR plate. The percentage of inhibition or decrease of HCV RNA level due to compound treatment was calculated using the DMSO or no compound control as 0% of inhibition. The IC50 (concentration at which 50% inhibition of HCV RNA level is observed) was calculated from the titration curve of any given compound.

The IC50 values inhibitory activity of some of the compounds of the present invention is shown in Table 1 above.

EXAMPLE 8

The Ki determinations were performed as follows. The Ki values for some compounds of the present invention are recited above in Table 1.

HPLC Microbore Method for Separation of 5AB Substrate and Products Substrate $NH_2$-Glu-Asp-Val-Val-(alpha)Abu-Cys-Ser-Met-Ser-Tyr-COOH Stock solution of 20 mM 5AB was made in DMSO w/0.2M DTT. This was stored in aliquots at −20 C.

Buffer: 50 mM HEPES, pH 7.8; 20% glycerol; 100 mM NaCl Total assay volume was 200 μL

|  | X1 (μL) | Conc. in assay |
| --- | --- | --- |
| Buffer | 155 | see above |
| 5 mM KK4A | 1 | 25 μM |
| 1 M DTT | 1 | 5 mM |
| DMSO or inhibitor | 3 | 1.5% v/v |
| 0.25 μM tNS3 | 20 | 25 nM |
| 200 μM SAB (initiate) | 20 | 20 μM |

The buffer was combined with KK4A, DTT, and tNS3; 177 μL of this solution was distributed each into wells of 96 well plate and incubated at 30° C. for ~5–10 min.

3 μL of appropriate concentration of test compound dissolved in DMSO (DMSO only for control) was added to each well and incubate at 30° C. for 15 min.

Reaction was initiated by addition of 20 μL of 200 μM 5AB substrate (20 μM concentration is equivalent or slightly lower than the Km for 5AB) and incubated for 20 min at 30° C. The reaction was terminated by addition of 50 μL of 10% TFA 200 μL aliquots were transferred to HPLC vials The SMSY product was isolated from substrate and KK4A by the method which follows.

Microbore Separation Method

Instrumentation:

Hewlett Packard 1100

Degasser G1322A

Binary pump G1312A

Autosampler G1313A

Column themostated chamber G1316A

Diode array detector G1315A

Column: Phenomenex Jupiter; 5 micron C18; 300 angstroms;

150×2 mm; P/O 00F-4053-B0

Column thermostat: 40° C.

Injection volume: 100 μL

Solvent A=HPLC grade water+0.1% TFA

Solvent B=HPLC grade acetonitrile+0.1% TFA

| Time (min) | % B | Flow (ml/min) | Max press. |
| --- | --- | --- | --- |
| 0 | 5 | 0.2 | 400 |
| 12 | 60 | 0.2 | 400 |
| 13 | 100 | 0.2 | 400 |
| 16 | 100 | 0.2 | 400 |
| 17 | 5 | 0.2 | 400 |

Stop time: 17 min

Post-run time: 10 min

What is claimed is:
1. A compound of the formula (I):

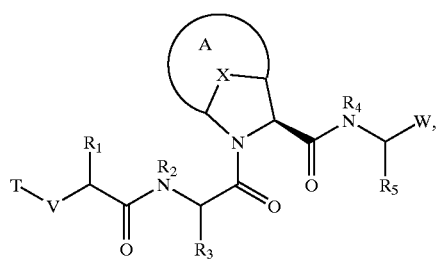

wherein:
A, together with X and the atoms to which X is bound, is a 4- to 7-membered aromatic or non-aromatic ring having up to 4 heteroatoms independently selected from N, NH, O, SO, or $SO_2$; wherein said ring is optionally fused to a (C6–C10)aryl, (C5–C10)heteroaryl, (C3–C10)cycloalkyl or (C3–C10)heterocyclyl; wherein A has up to 3 substituents selected independently from J;

X is —$[CH_2]_o$—, —$[CJ'J']_o$—, —$[CH_2]_m$—O—, —$[CH_2]_m$—$S(O)_2$—, —$[CH_2]_m$—SO—, —$[CH_2]_m$—S—, —$[CR_{20}R_{20}]_m$—$NR_{21}$—, or —$[CR_{20}R_{20}]_m$—NJ"—, wherein:

$R_{21}$ is hydrogen or —C(O)—O—$R_{22}$;
o is 1 or 2;
$R_{22}$ is —(C1–C6)alkyl, —(C2–C6)alkenyl, or —(C2–C6)alkynyl;
m is 0 or 1;

J is halogen, —OR', —$NO_2$, —$CF_3$, —$OCF_3$, —R', oxo, —OR', —O-benzyl, —O-phenyl, 1,2-methylenedioxy, —$N(R')_2$, —SR', —SOR', —$SO_2R'$, —C(O)R', —COOR', or —$CON(R')_2$;

J' is halogen, —OR', —$NO_2$, —$CF_3$, —$OCF_3$, —R', —OR', —O-benzyl, —O-phenyl, 1,2-methylenedioxy, —$N(R')_2$, —SR', —SOR', —$SO_2R'$, —C(O)R', —COOR', or —$CON(R')_2$;

J" is —OR', —$CF_3$, —$OCF_3$, —R', oxo, —OR', —O-benzyl, —O-phenyl, 1,2-methylenedioxy, —$N(R')_2$, —SR', —SOR', —$SO_2R'$, —C(O)R', —COOR', or —$CON(R')_2$, wherein each R' is independently:
hydrogen,
—(C1–C12)aliphatic,
—(C3–C10)cycloalkyl or -cycloalkenyl,
—(C1–C12)aliphatic-[(C3–C10)cycloalkyl or -cycloalkenyl],
—(C6–C10)aryl,
—(C1–C12)aliphatic-(C6–C10)aryl,
—(C3–C10)heterocyclyl,
—(C1–C12)aliphatic-(C6–C10)heterocyclyl,
—(C5–C10)-heteroaryl, or
—(C1–C12)-aliphatic-(C5–C10)heteroaryl;

$R_1$ and $R_3$ are independently:
—(C1–C12)aliphatic,
—(C3–C10)-cycloalkyl or -cycloalkenyl,
—(C1–C12)-aliphatic-[(C3–C10)-cycloalkyl or -cycloalkenyl],
—(C6–C10)-aryl,
(C1–C12)aliphatic-(C6–C10)aryl,
—(C3–C10)-heterocyclyl,
—(C1–C12)aliphatic-(C6–C10)heterocyclyl,
—(C5–C10)heteroaryl, or
—(C1–C12)aliphatic-(C5–C10)heteroaryl,
wherein each of $R_1$ and $R_3$ is independently and optionally substituted with up to 3 substituents independently selected from J;
wherein up to 3 aliphatic carbon atoms in $R_1$ and $R_3$ may be replaced by a heteroatom selected from O, NH, S, SO, and $SO_2$ in a chemically stable arrangement;

$R_2$ and $R_4$ are independently
hydrogen,
—(C1–C12)aliphatic,
—(C1–C12)aliphatic-(C3–C10)cycloalkyl, or
—(C1–C12)aliphatic-(C6–C10)aryl,
wherein each of $R_2$ and $R_4$ is independently and optionally substituted with up to 3 substituents independently selected from J;
wherein up to two aliphatic carbon atoms in $R_2$ and $R_4$ may be replaced by a heteroatom selected from O, NH, S, SO, and $SO_2$;

$R_5$ is —(C1–C12)aliphatic, wherein any hydrogen is optionally replaced with halogen, and wherein any hydrogen or halogen atom bound to any terminal carbon atom of $R_5$ is optionally substituted with sulfhydryl or hydroxy;

W is: —C(O)OH;

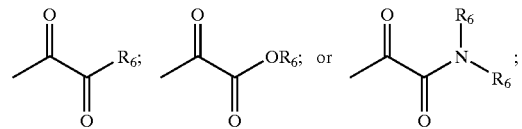

wherein each $R_6$ is independently:
hydrogen,
—(C1–C12)aliphatic,
—(C6–C10)aryl,
—(C6–C10)aryl-(C1–C12)aliphatic,
—(C3–C10)-cycloalkyl or -cycloalkenyl,
—(C1–C12)-aliphatic-[(C3–C10)-cycloalkyl or -cycloalkenyl],
—(C3–C10)heterocyclyl,
—(C3–C10)heterocyclyl-(C1–C12)aliphatic,
—(C5–C10)heteroaryl, or
—(C1–C12)aliphatic-(C5–C10)heteroaryl, or
two $R_6$ groups, which are bound to the same nitrogen atom, form together with that nitrogen atom, a —(C3–C10)heterocyclic ring;
wherein $R_6$ is optionally substituted with up to 3 J substituents or with a suitable electron withdrawing group;

V is —$C(O)N(R_8)$—, —$S(O)N(R_8)$—, —$S(O)_2N(R_8)$—, a bond, —$CH(R_8)$—, —$N(R_8)$—, —O—, —O—CH$(R_8)$—, —S—, —S—CH$(R_8)$, —C(O)—, —C(O)—O—, —C(O)—S—, —C(O)—$CHR_8$—, —S(O)—, —S(O)—$CH(R_8)$, —S(O)—$N(R_8)$—$CHR_8$, —$S(O)_2$—, —S—$(O)_2$—$CH(R_8)$—, or —$S(O)_2$—N$(R_8)$—$CHR_8$;
wherein $R_8$ is hydrogen or —(C1–C12)aliphatic;

T is:
—(C6–C10)aryl,
—(C1–C12)aliphatic-(C6–C10)aryl,
—(C3–C10)-cycloalkyl or -cycloalkenyl,
—(C1–C12)aliphatic-[(C3–C10)-cycloalkyl or -cycloalkenyl], —(C3–C10)heterocyclyl,
—(C1–C12)aliphatic-(C3–C10)heterocyclyl,
—(C5–C10)heteroaryl, or
—(C1–C12)aliphatic-(C5–C10)heteroaryl; or T is:

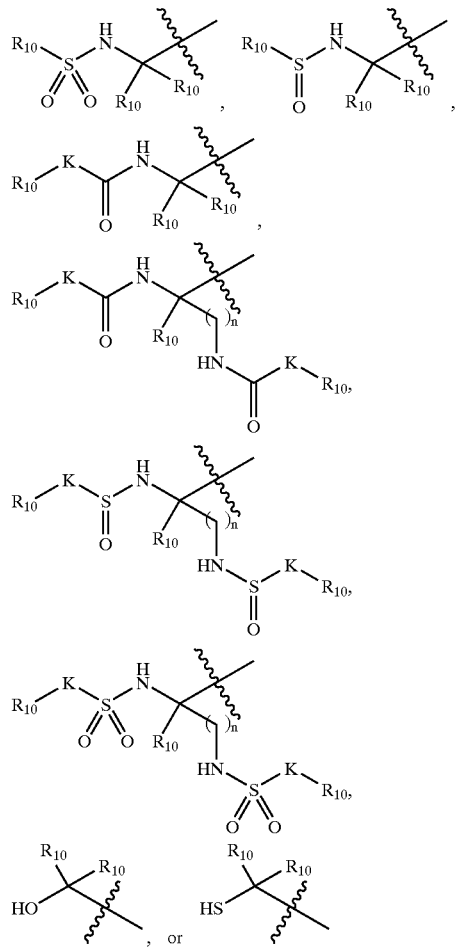

wherein:
R$_{10}$ is:
hydrogen,
—(C1–C12)aliphatic,
—(C6–C10)aryl,
—(C1–C12)aliphatic-(C6–C10)aryl,
—(C3–C10)-cycloalkyl or -cycloalkenyl,
—(C1–C12)aliphatic-[(C3–C10)-cycloalkyl or -cycloalkenyl],
—(C3–C10)heterocyclyl,
—(C1–C12)aliphatic-(C3–C10)heterocyclyl,
—(C5–C10)heteroaryl, or
—(C1–C12)aliphatic-(C5–C10)heteroaryl,
wherein each T is optionally substituted with up to 3 J substituents;
K is a bond, —(C1–C12)aliphatic, —O—, —S—, —NR$_9$—, —C(O)—, or —C(O)—NR$_9$—, wherein R$_9$ is hydrogen or —(C1–C12)aliphatic;
n is 1–3; and
each R$_{20}$ is independently hydrogen, —(C1–C6)aliphatic or —O—((C1–C6)aliphatic); or each R$_{20}$ is taken together with the carbon atoms to which they are bound to form a (C3–C6)cycloalkyl.

2. The compound according to claim 1, wherein the compound of formula (I):

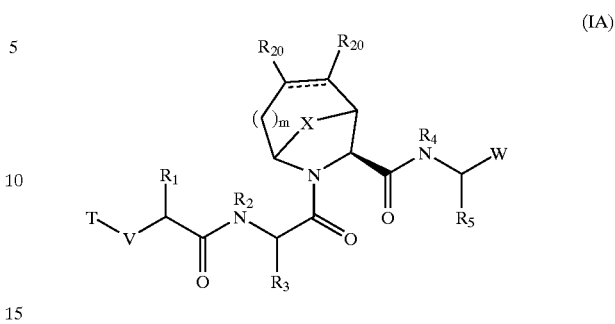

wherein the variables are as defined above.

3. The compound according to claim 1 or claim 2, wherein:

X is —[CH$_2$]$_o$—, —[CH$_2$]$_m$—O—, —[CH$_2$]$_m$—S(O)$_2$, or —[CR$_{20}$R$_{20}$]$_m$—NR$_{21}$; wherein:
R$_{21}$ is hydrogen or —C(O)—O—R$_{22}$;
o is 1 or 2;
R$_{22}$ is —(C1–C6)alkyl, —(C2–C6)alkenyl, or —(C2–C6)alkynyl;
m is 0 or 1;
R$_5$ is —(C2–C7)alkyl optionally substituted with halogen;
each R$_{20}$ is independently hydrogen, —(C1–C6)alkyl or —O—((C1–C6)alkyl); or each R$_{20}$ is taken together with the carbon atoms to which they are bound to form a (C$_3$–C$_6$) cycloalkyl;
R$_3$ and R$_1$ are independently —(C1–C10)alkyl, —(C3–C7)cycloalkyl, or —((C1–C6)alkyl)—((C$_3$–C$_7$)cycloalkyl);
V is a bond, —CH(R$_8$)—, —N(R$_8$)—, —O—, —O—CH(R$_8$), —S—, —S—CH(R$_8$), —C(O)—, —C(O)—O—, —C(O)—S—, —C(O)—CHR$_8$—, —C(O)N(R$_8$)—, —S(O)—, —S(O)—CH(R$_8$)—, —S(O)N(R$_8$)—, —S(O)—N(R$_8$)—CHR$_8$, —S(O)$_2$, —S—(O)$_2$—CH (R$_8$)—, —S(O)$_2$N(R$_8$)—, or —S(O)$_2$—N(R$_8$)—CHR$_8$;
wherein R$_8$ is hydrogen or —(C1–C3)alkyl;
T is —(C6–C10)aryl, —(C5–C10)heteroaryl, —(C3–C6) cycloalkyl, —(C3–C10)heterocyclyl, —(C1–C6)alkyl-(C6–C10)aryl, —(C1–C6)alkyl-(C5–C10heteroaryl, —(C1–C6)alkyl-(C3–C6)cycloalkyl, —(C1–C6)alkyl-(C3–C10)heterocyclyl, —(C2–C6)alkenyl-(C6–C10)aryl, —(C2–C6)alkenyl-(C5–C10)heteroaryl, —(C2–C6)alkenyl-(C3–C6)cycloalkyl, —(C2–C6) alkenyl-(C3–C10)heterocyclyl,

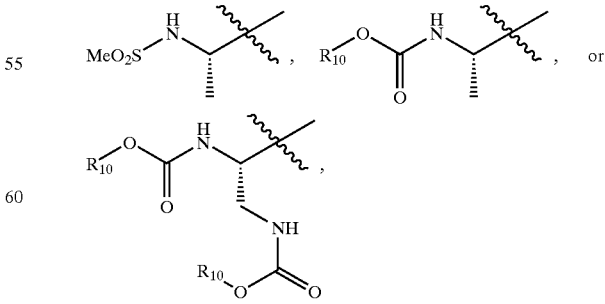

wherein:
R$_{10}$ is —(C1–C4)alkyl; and

W is —C(O)OH or —C(O)—C(O)—R$_6$, wherein:
   R$_6$ is —(C1–C6)alkyl, —(C6–C10)aryl, —(C3–C6)cycloalkyl, —(C5–C10)heteroaryl, —(C3–C10)heterocyclyl, or
W is —C(O)—C(O)NR$_6$R$_6$, wherein:
   NR$_6$R$_6$ is —NH—((C1–C6)alkyl), —NH—((C3–C6)cycloalkyl), —NH—CH(CH$_3$)-aryl, —NH—CH(CH$_3$)—(C5–C10)heteroaryl or —NH—CH(CH$_3$)—(C3–C10)heterocyclyl, wherein said aryl, heteroaryl, or heterocyclyl is optionally substituted with a suitable electron withdrawing group.

4. The compound according to claim 3, wherein V is —NH—.

5. The compound according to claim 3, wherein V is —C(O)—.

6. The compound according to claim 3, wherein T is a —(C5–C10)heteroaryl.

7. The compound according to claim 6, wherein T is:

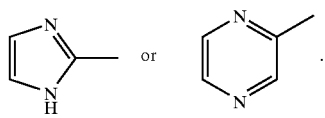

8. The compound according to claim 3, wherein R$_1$ is —CH$_2$—CH(CH$_3$)—CH$_3$, —C(CH$_3$)$_3$, —CH(CH$_3$)$_2$, —CH(CH$_3$)—CH$_2$—CH$_3$, or cyclohexyl.

9. The compound according to claim 8, wherein R$_1$ is cyclohexyl.

10. The compound according to claim 3, wherein R$_3$ is —C(CH$_3$)$_2$, —CH(CH$_3$)$_2$, —CH(CH$_3$)—CH$_2$—CH$_3$, or cyclohexyl.

11. The compound according to claim 10, wherein R$_3$ is —C(CH$_3$)$_3$ or —CH(CH$_3$)$_2$.

12. The compound according to claim 3, wherein each R$_{20}$ is independently —CH$_3$ or hydrogen.

13. The compound according to claim 12, wherein each R$_{20}$ is hydrogen.

14. The compound according to claim 3, wherein R$_5$ is —CH$_2$CH$_2$CH$_3$, —CH$_2$CH$_2$CH$_2$CH$_3$, —CH$_2$CH$_2$CH$_2$F, —CH$_2$CH$_2$CHF$_2$, or —CH$_2$CH$_2$CF$_3$.

15. The compound according to claim 14, wherein R$_5$ is —CH$_2$CH$_2$CH$_2$CH$_3$ or —CH$_2$CH$_2$CHF$_2$.

16. The compound according to claim 15, wherein R$_5$ is —CH$_2$CH$_2$CH$_2$CH$_3$.

17. The compound according to claim 3, wherein W is C(O)—C(O)—R$_6$.

18. The compound according to claim 3, wherein W is C(O)—C(O)NR$_6$R$_6$ and NR$_6$R$_6$ is —NH—(C3–C6)cycloalkyl, —NH—CH(CH$_3$)—(C6–C10)aryl, —NH—CH(CH$_3$)—(C3–C10) heterocyclyl, or —NH—CH(CH$_3$)—(C5–C10)heteroaryl, wherein said aryl, heterocyclyl, or heteroaryl is optionally substituted with halogen.

19. The compound according to claim 18, wherein NR$_6$R$_6$ is:

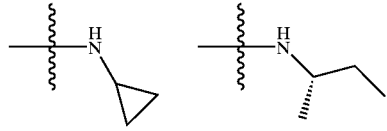

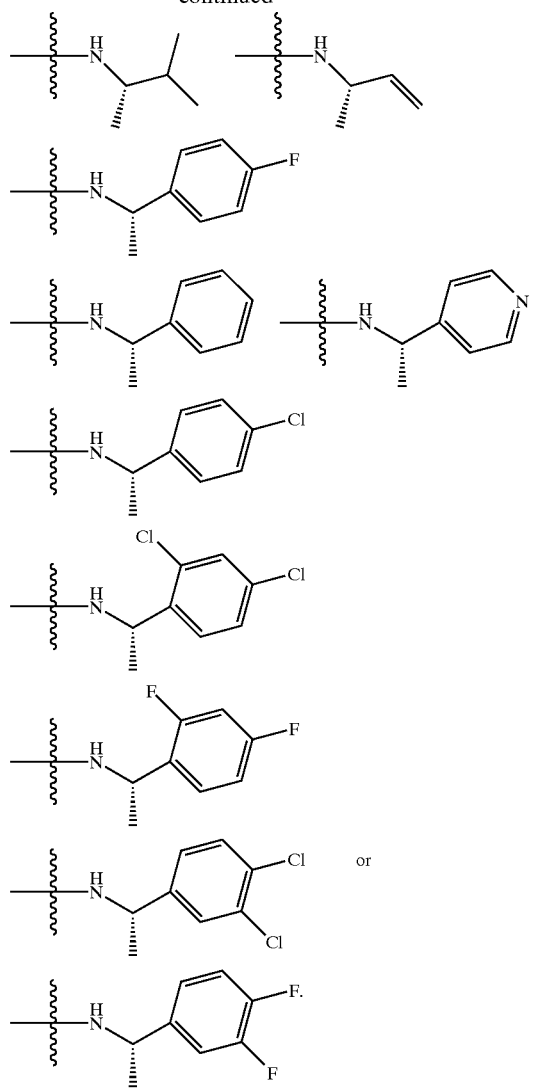

20. The compound according to claim 19, wherein NR$_6$R$_6$ is:

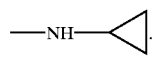

21. The compound according to claim 1 or claim 2, wherein T contains at least one hydrogen bond donor moiety selected from —NH$_2$, —NH—, —OH, and —SH.

22. The compound according to claim 21, wherein T is:

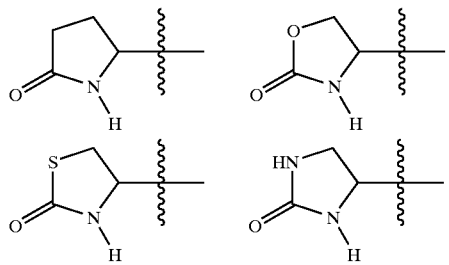

-continued
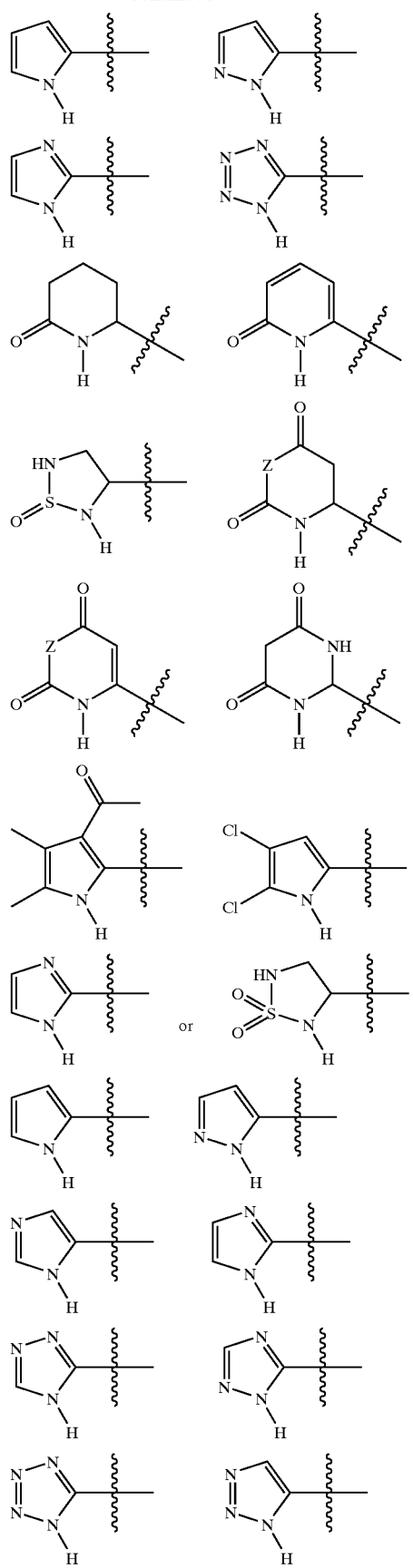
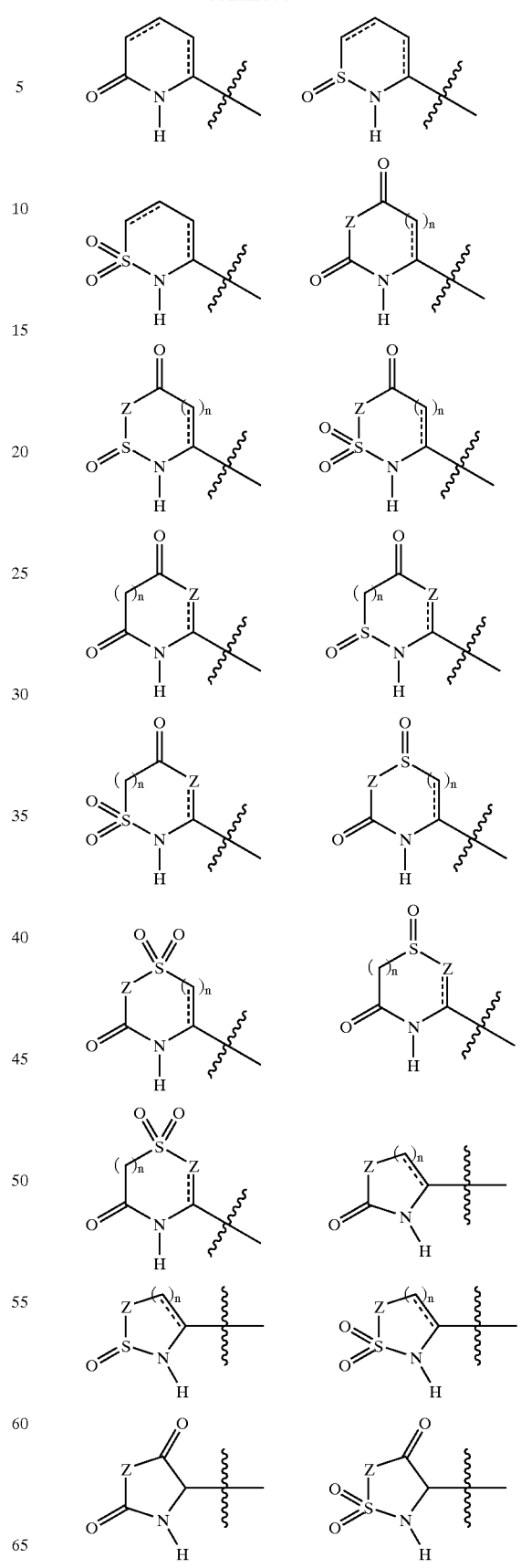

-continued
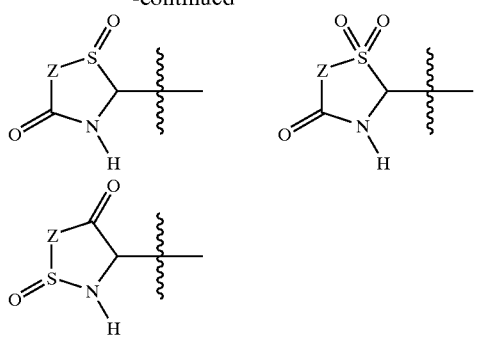
wherein:
T is optionally substituted with up to 3 J substituents, wherein J is as defined in claim 1;
Z is independently O, S, $NR_{10}$, or $C(R_{10})_2$;
n is independently 1 or 2; and
═══ is independently a single bond or a double bond.
23. The compound according to claim 22, wherein T is:
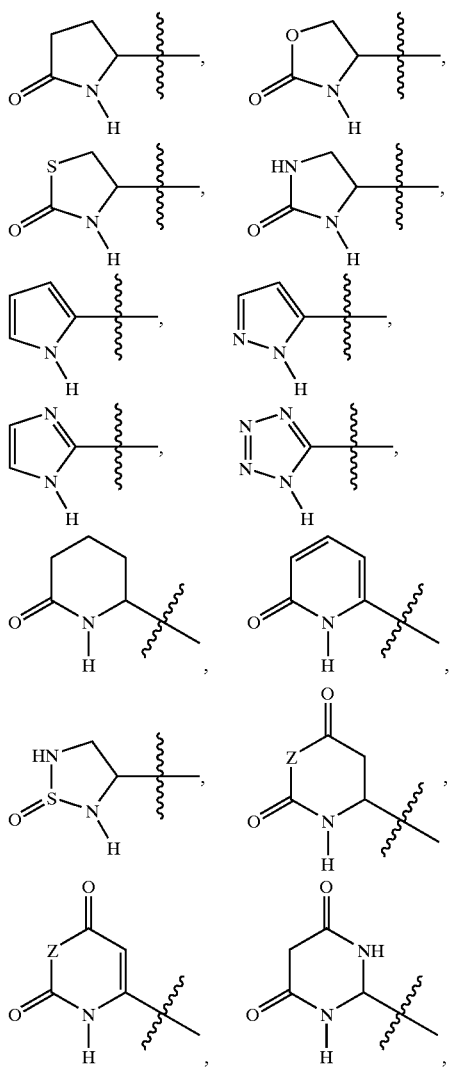
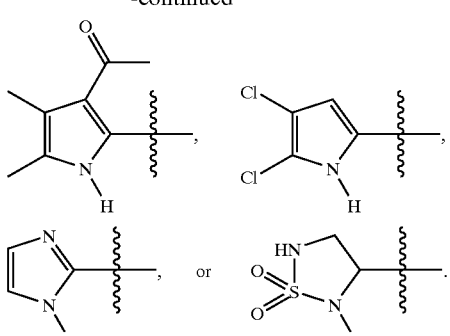
24. The compound according to claim 23, wherein T is
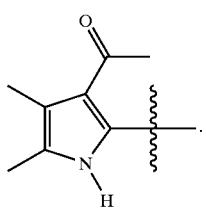
25. The compound according to claim 21, wherein T is:
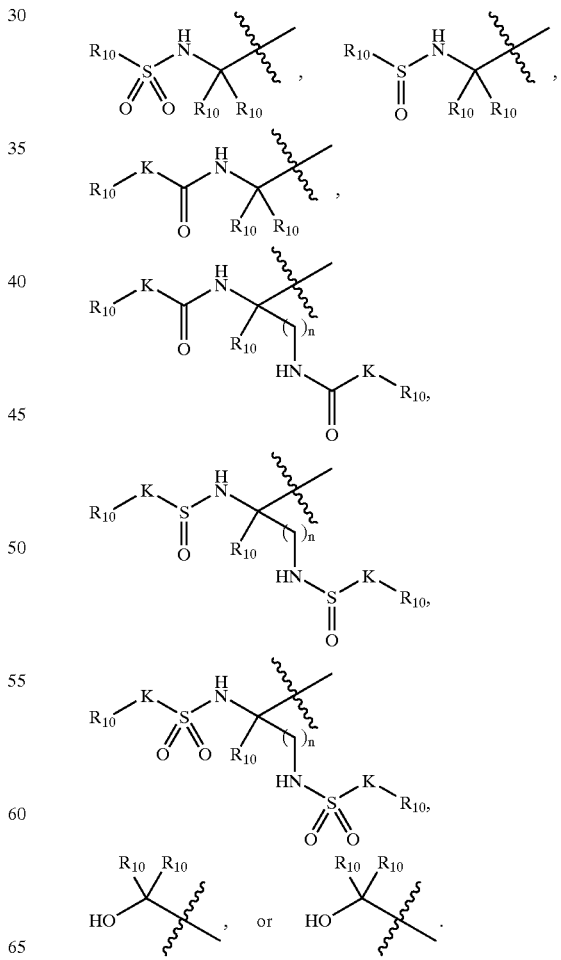

26. The compound according to claim 25, wherein T is:

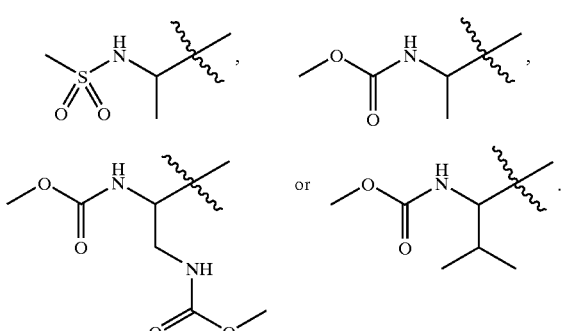

27. The compound according to claim 1 or claim 2, wherein $R_1$ is:

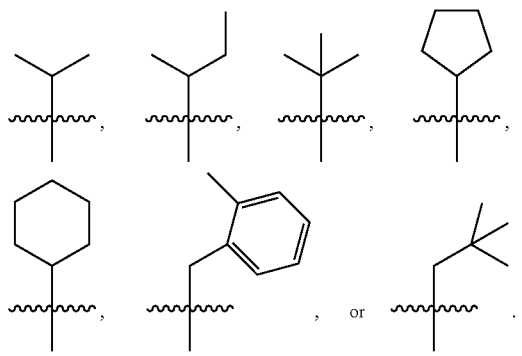

28. The compound according to claim 27, wherein $R_1$ is:

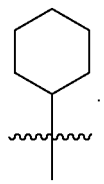

29. The compound according to claim 1 or claim 2, wherein $R_3$ is:

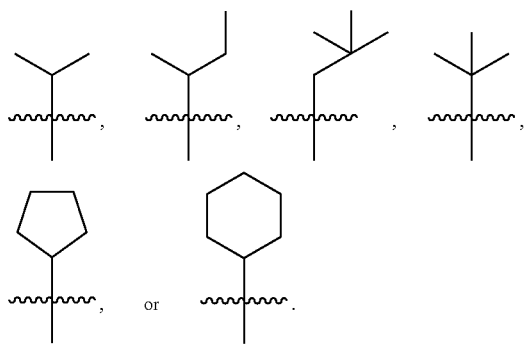

30. The compound according to claim 29, wherein $R_3$ is:

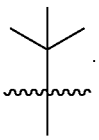

31. The compound according to claim 1 or claim 2, wherein $R_5$ is:

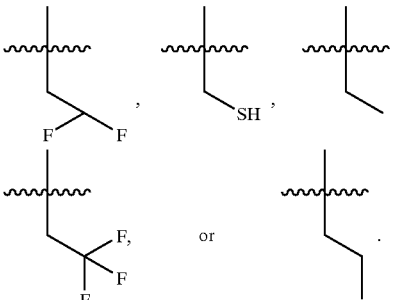

32. The compound according to claim 31, wherein $R_5$ is:

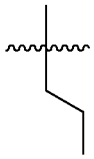

33. The compound according to claim 1 or claim 2, wherein $R_2$ and $R_4$ are each independently H, methyl, ethyl, or propyl.

34. The compound according to claim 33, wherein $R_2$ and $R_4$ are each H.

35. The compound according to claim 1 or 2, wherein X is $-[CH_2]_o-$, $-[CJJ']_o-$, $-[CH_2]_m-O-$, $-[CH_2]_m-S(O)_2-$, $-[CH_2]_m-SO-$, $-[CR_{20}R_{20}]_m-NR_{21}-$, or $-[CR_{20}R_{20}]_m-NJ''-$.

36. A composition comprising a compound according to any one of claims 1–35 or a pharmaceutically acceptable salt, derivative or prodrug thereof in an amount effective to inhibit a serine protease; and a acceptable carrier, adjuvant or vehicle.

37. The composition according to claim 36, wherein said composition is formulated for administration to a patient.

38. The composition according to claim 37, wherein said composition comprises an additional agent selected from an immunomodulatory agent; an antiviral agent; a second inhibitor of HCV protease; an inhibitor of another target in the HCV life cycle; or combinations thereof.

39. The composition according to claim 38, wherein said immunomodulatory agent is α-, β-, or γ-interferon; the antiviral agent is ribavarin or amantadine; or the inhibitor of another target in the HCV life cycle is an inhibitor of HCV helicase, polymerase, or metalloprotease.

40. A method of inhibiting the activity of a serine protease comprising the step of contacting said serine protease with a compound according to any one of claims 1–35.

41. The method according to claim 40, wherein said protease is an HCV NS3 protease.

42. A method of treating an HCV infection in a patient comprising the step of administering to said patient a composition according to claim 37 or claim 38.

43. The method according to claim 42, comprising the additional step of administering to said patient an additional agent selected from an immunomodulatory agent; an antiviral agent; a second inhibitor of HCV protease; an inhibitor of another target in the HCV life cycle; or combinations thereof; wherein said additional agent is administered to said patient as part of said composition according to claim 37 or as a separate dosage form.

44. The method according to claim 43, wherein said immunomodulatory agent is α-, β-, or γ-interferon; said antiviral agent is ribavarin or amantadine; or said inhibitor of another target in the HCV life cycle is an inhibitor of HCV helicase, polymerase, or metalloprotease.

45. A method of eliminating or reducing HCV contamination of a biological sample or medical or laboratory equipment, comprising the step of contacting said biological sample or medical or laboratory equipment with a composition according to claim 36.

46. The method according to claim 45, wherein said sample or equipment is selected from blood, body fluids other than blood, biological tissue, a surgical instrument, a surgical garment, a laboratory instrument, a laboratory garment, a blood or other bodily fluid collection apparatus; a blood or other bodily fluid storage material.

* * * * *